(12) United States Patent
Omori et al.

(10) Patent No.: US 10,993,607 B2
(45) Date of Patent: May 4, 2021

(54) ENDOSCOPE APPARATUS AND METHOD OF OPERATING ENDOSCOPE APPARATUS

(71) Applicant: FUJIFILM Corporation, Tokyo (JP)

(72) Inventors: Toshihiko Omori, Kanagawa (JP); Makoto Sugizaki, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 617 days.

(21) Appl. No.: 15/828,376

(22) Filed: Nov. 30, 2017

(65) Prior Publication Data

US 2018/0153386 A1 Jun. 7, 2018

(30) Foreign Application Priority Data

Dec. 2, 2016 (JP) .............................. JP2016-235212

(51) Int. Cl.
*A61B 1/04* (2006.01)
*A61B 1/06* (2006.01)
(Continued)

(52) U.S. Cl.
CPC ............ *A61B 1/043* (2013.01); *A61B 1/0005* (2013.01); *A61B 1/0051* (2013.01); *A61B 1/00186* (2013.01); *A61B 1/0638* (2013.01); *A61B 1/00009* (2013.01); *A61B 1/00013* (2013.01); *A61B 1/042* (2013.01); *A61B 1/0684* (2013.01);
(Continued)

(58) Field of Classification Search
CPC ....... A61B 1/043; A61B 1/0638; A61B 1/646; G01N 21/26
See application file for complete search history.

(56) References Cited

U.S. PATENT DOCUMENTS 6,899,675 B2  5/2005 Cline et al.
8,767,059 B2  7/2014 Endo et al.
(Continued)

FOREIGN PATENT DOCUMENTS

JP 2005514147 5/2005
JP 2008043383 2/2008
(Continued)

OTHER PUBLICATIONS

"Office Action of Japan Counterpart Application," with English translation thereof, dated Jan. 7, 2020, p. 1-p. 8.

*Primary Examiner* — Matthew J Kasztejna
(74) *Attorney, Agent, or Firm* — JCIPRNET

(57) ABSTRACT

An endoscope apparatus and a method of operating the endoscope apparatus that perform both illumination light observation and fluorescence observation by a simple configuration. At least a part of a wavelength region of excitation light is included in a first wavelength region where the absorption intensity of a fluorescent material is 10% or more of a first peak value. The wavelength region of the excitation light is included in a second wavelength region where the transmittance of a first spectral transmittance characteristic is 60% or more of a second peak value and a third wavelength region where the transmittance of a second spectral transmittance characteristic is 40% or less of a third peak value. A wavelength at which intensity of fluorescence is a peak is included in a fourth wavelength region where the transmittance of the second spectral transmittance characteristic is 80% or more of the third peak value.

20 Claims, 27 Drawing Sheets

(51) Int. Cl.
    *A61B 1/005*     (2006.01)
    *A61B 1/00*     (2006.01)
    *G01N 21/64*     (2006.01)

(52) U.S. Cl.
    CPC ......... *G01N 21/64* (2013.01); *G01N 21/6456* (2013.01); *G06T 2207/10068* (2013.01)

(56) References Cited

U.S. PATENT DOCUMENTS

| | | | |
|---|---|---|---|
| 2004/0225222 A1* | 11/2004 | Zeng | A61B 1/0676 600/476 |
| 2010/0245552 A1* | 9/2010 | Higuchi | A61B 1/0638 348/68 |
| 2013/0012864 A1* | 1/2013 | Kubo | A61B 1/041 604/20 |
| 2015/0087903 A1* | 3/2015 | Kuramoto | A61B 1/00006 600/109 |
| 2015/0381909 A1* | 12/2015 | Butte | A61B 1/00186 348/68 |
| 2016/0262622 A1* | 9/2016 | Ishihara | A61B 1/04 |
| 2017/0020377 A1 | 1/2017 | Takeuchi et al. | |

FOREIGN PATENT DOCUMENTS

| | | |
|---|---|---|
| JP | 2011092683 | 5/2011 |
| JP | 2011104333 | 6/2011 |
| WO | 2015156153 | 10/2015 |

\* cited by examiner

FIG. 29

| EXAMPLE COMPARATIVE EXAMPLE | SUPPLEMENT | FLUORESCENT DYE | PEAK WAVELENGTH OF EXCITATION LIGHT | CONTRIBUTE TO (B) | CONTRIBUTE TO (A) | | | | (A) SENSOR COLOR SEPARATION | (B) FLUORESCENCE EMISSION INTENSITY | (C) VISUAL PERFORMANCE OF FLUORESCENCE IMAGE |
|---|---|---|---|---|---|---|---|---|---|---|---|
| | | | | CONDITION OF FIRST WAVELENGTH REGION | CONDITION OF SECOND WAVELENGTH REGION | CONDITION OF THIRD WAVELENGTH REGION | CONDITION OF FOURTH WAVELENGTH REGION | | | | |
| 1 | LIGHT SOURCE A SENSOR A | FLUORESCEIN | 410nm | 10% OR MORE | 60% OR MORE | 10% OR LESS | 80% OR MORE | good | pass | pass |
| 2 (COMPARATIVE EXAMPLE) | V LIGHT OF LIGHT SOURCE A SENSOR C | FLUORESCEIN | 410nm | 10% OR MORE | LESS THAN 60% | 10% OR LESS | 80% OR MORE | fail | pass | fail |
| 3 | V LIGHT OF LIGHT SOURCE B SENSOR B | FLUORESCEIN | 410nm | 10% OR MORE | 60% OR MORE | 20% OR LESS | 80% OR MORE | pass | pass | pass |
| 4 | BL1 LIGHT OF LIGHT SOURCE B SENSOR B | FLUORESCEIN | 450nm | 50% OR MORE | 60% OR MORE | 40% OR LESS | 80% OR MORE | pass | good | good |
| 5 | BL1 LIGHT OF LIGHT SOURCE B SENSOR A | FLUORESCEIN | 450nm | 50% OR MORE | 80% OR MORE | 20% OR LESS | 80% OR MORE | good | good | very good |
| 6 (COMPARATIVE EXAMPLE) | BL1 LIGHT OF LIGHT SOURCE B SENSOR C | FLUORESCEIN | 450nm | 50% OR MORE | 80% OR MORE | 10% OR LESS | 80% OR MORE | fail | good | fail |
| 7 (COMPARATIVE EXAMPLE) | BL1 LIGHT OF LIGHT SOURCE B SENSOR D | FLUORESCEIN | 450nm | 50% OR MORE | LESS THAN 60% | 10% OR LESS | 80% OR MORE | fail | good | fail |
| 8 | BL1 LIGHT AND BL2 LIGHT SENSOR A | FLUORESCEIN | 460nm | 50% OR MORE | 80% OR MORE | 40% OR LESS | 80% OR MORE | pass | very good | very good |
| 9 (COMPARATIVE EXAMPLE) | LED LIGHT OF 400nm SENSOR A | FLUORESCEIN | 400nm | LESS THAN 10% | 60% OR MORE | 20% OR LESS | LESS THAN 80% | good | fail | fail |
| 10 (COMPARATIVE EXAMPLE) | LED LIGHT OF 490nm SENSOR B | FLUORESCEIN | 490nm | 50% OR MORE | 60% OR MORE | LARGER THAN 40% | 80% OR MORE | fail | good | fail |
| 11 (COMPARATIVE EXAMPLE) | LED LIGHT OF 490nm SENSOR A | FLUORESCEIN | 490nm | 50% OR MORE | 80% OR MORE | 60% OR MORE | 80% OR MORE | fail | good | fail |

FIG. 30

| EXAMPLE COMPARATIVE EXAMPLE | SUPPLEMENT | FLUORESCENT DYE | PEAK WAVELENGTH OF EXCITATION LIGHT | CONTRIBUTE TO (B) | CONTRIBUTE TO (A) | | | (A) SENSOR COLOR SEPARATION | (B) FLUORESCENCE EMISSION INTENSITY | (C) VISUAL PERFORMANCE OF FLUORESCENCE IMAGE |
|---|---|---|---|---|---|---|---|---|---|---|
| | | | | CONDITION OF FIRST WAVELENGTH REGION | CONDITION OF SECOND WAVELENGTH REGION | CONDITION OF THIRD WAVELENGTH REGION | CONDITION OF FOURTH WAVELENGTH REGION | | | |
| 12-22 | SAME AS 1 TO 11 | RHODAMINE GREEN | | SAME AS 1 TO 11 | | | | SAME AS A TO H | | |
| 23 | V LIGHT OF LIGHT SOURCE B AND SENSOR B | PpIX | 410nm | 50% OR MORE | 60% OR MORE | 10% OR LESS | 80% OR MORE | good | very good | very good |
| 24 (COMPARATIVE EXAMPLE) | BL LIGHT OF LIGHT SOURCE B AND SENSOR B | PpIX | 450nm | LESS THAN 10% | 80% OR MORE | 10% OR LESS | 80% OR MORE | very good | fail | fail |
| 25 | V LIGHT OF LIGHT SOURCE B AND SENSOR B | PpIX | 410nm | 50% OR MORE | 60% OR MORE | 20% OR LESS | 80% OR MORE | pass | very good | good |
| 26 (COMPARATIVE EXAMPLE) | G(520 TO 550nm) LED AND SENSOR A | SYPRO RED | 520 TO 550nm | 50% OR MORE | 80% OR MORE | LARGER THAN 40% | 80% OR MORE | fail | very good | fail |
| 27 | G(520 TO 550nm) LED FILTER AND SENSOR A | SYPRO RED | 550nm | 50% OR MORE | 80% OR MORE | 10% OR LESS | 80% OR MORE | very good | very good | very good |

ENDOSCOPE APPARATUS AND METHOD OF OPERATING ENDOSCOPE APPARATUS

CROSS-REFERENCE TO RELATED APPLICATIONS

The present application claims priority under 35 U.S.C. § 119 to Japanese Patent Application No. 2016-235212, filed on Dec. 2, 2016. The above application is hereby expressly incorporated by reference, in its entirety, into the present application.

BACKGROUND OF THE INVENTION

1. Field of the Invention

The present invention relates to an endoscope apparatus that performs illumination light observation and fluorescence observation and a method of operating the endoscope apparatus.

2. Description of the Related Art

In the past, an endoscopy using an electronic endoscope (hereinafter, simply abbreviated as an endoscope) has been performed in the field of medicine. In the endoscopy, for example, a portion to be observed (referred to as a target portion) in a subject is irradiated with, for example, white light as illumination light and the normal observation (illumination observation) of the portion to be observed is performed on the basis of a reflected-light image that is acquired from the image pickup using reflected light of the white light reflected from the portion to be observed.

Further, in recent years, fluorescence observation has been performed as an endoscopy in addition to normal observation. A portion to be observed is irradiated with excitation light to allow a fluorescent material, which is contained in the portion to be observed, to be excited and to emit light, and the fluorescence observation of the portion to be observed is performed on the basis of a fluorescence image that is acquired from the image pickup using fluorescence generated from the fluorescent material. Particularly, in recent years, a material, which emits fluorescence in response to a cancer-specific material or environment or is selectively accumulated on a cancer, has been labeled in advance by a fluorescent dye (fluorescent material), so that the use of fluorescence observation has been expected for various purposes, such as the early detection of a cancer, the prevention of oversight of a cancer, and the prevention of the leaving of a cancer at the time of excision of a cancer, using fluorescence observation.

The fluorescent dye absorbs excitation light of a certain wavelength region, and emits fluorescence of a wavelength region in which wavelength is longer than wavelength in the wavelength region. For example, since fluorescein, of which the use for medical angiography is approved, has an absorption peak of excitation light near a wavelength of 490 nm and has a fluorescence peak near a wavelength of 520 nm, fluorescein absorbs blue light and emits green light.

Here, a wavelength difference between the absorption peak and the fluorescence peak described above is referred to as Stokes shift, and Stokes shift varies depending on the type of a fluorescent material. Since it is difficult to distinguish excitation light from fluorescence in a case in which Stokes shift is small, it is not possible to accurately detect fluorescence. For this reason, a dichroic filter, a band pass filter, a long-pass filter, or the like is used in the fluorescence observation as a filter for fluorescence observation that reflects or transmits light of a specific wavelength region corresponding to excitation light or fluorescence. For example, it is considered that the fluorescence observation of the above-mentioned fluorescein is performed using a dichroic filter having small Stokes shift of about 30 nm, transmitting light having a wavelength of 500 nm or more, and blocking light of a wavelength region in which wavelength is shorter than a wavelength of 500 nm.

Incidentally, in a case in which fluorescence observation is performed by an endoscope, the above-mentioned filter for fluorescence observation needs to be disposed on the front side of an image pickup element provided in a tip portion of an insertion part of the endoscope. However, since the size and diameter of the tip portion are reduced, it is difficult to dispose the filter for fluorescence observation on the front side of the image pickup element. In addition, in a case in which both the normal observation and the fluorescence observation are performed by the endoscope, the filter for fluorescence observation is disposed on the front side of the image pickup element only in a case in which the fluorescence observation is performed and the filter for fluorescence observation needs to be retracted from the front side of the image pickup element in a case in which the normal observation is performed.

JP2011-104333A discloses an endoscope in which a filter for fluorescence observation is provided on a hood to be mounted on a tip portion of an insertion part of an endoscope and the hood for fluorescence observation is mounted on the tip portion to perform fluorescence observation. In a case in which the hood for fluorescence observation is removed from the tip portion of the insertion part of the endoscope, the above-mentioned normal observation can be performed by the endoscope disclosed in JP2011-104333A. That is, both normal observation and fluorescence observation can be performed without the disposition of the filter for fluorescence observation on the front side of the image pickup element in the tip portion.

On the other hand, JP2005-514147A discloses a fluorescence endoscope video system that includes an image pickup element for normal observation and an image pickup element for fluorescence observation separately provided in a tip portion thereof as in an endoscope apparatus for performing self-fluorescence observation. In the fluorescence endoscope video system disclosed in JP2005-514147A, color separation between excitation light and fluorescence is poor and overlap (cross talk) between the wavelength region of excitation light and the wavelength region of fluorescence occurs. Accordingly, a filter for reducing the intensity of excitation light is provided on the front side of the image pickup element to acquire a good fluorescence image.

SUMMARY OF THE INVENTION

However, in a case in which the insertion part of the endoscope is inserted into a subject to simultaneously perform fluorescence observation while performing normal observation in the endoscope disclosed in JP2011-104333A, the hood for fluorescence observation needs to be mounted on the tip portion of the insertion part of the endoscope and the insertion part needs to be inserted into a body again after the insertion part of the endoscope is removed from the subject once. Further, the same applies to a case in which the hood for fluorescence observation is mounted on the tip portion from the beginning. Accordingly, in a case in which normal observation is to be performed, the insertion part of the endoscope needs to be inserted into the subject again after the insertion part of the endoscope is removed from the subject once and the hood for the fluorescence observation is removed.

Furthermore, since light of a specific wavelength region is cut by the filter in a case in which the hood for fluorescence observation is mounted on the tip portion and a portion to be observed is irradiated with illumination light, such as white light, visibility deteriorates.

In the fluorescence endoscope video system disclosed in JP2005-514147A, a filter for reducing the intensity of excitation light needs to be provided on the front side of the image pickup element for fluorescence observation to obtain a good fluorescence image. However, since the size and diameter of the tip portion of the insertion part of the endoscope are reduced as already described, it is difficult to dispose the filter on the front side of the image pickup element. For this reason, there are problems that the structure of the tip portion is complicated and the diameter of the insertion part of the endoscope is increased in a case in which the filter is to be provided.

The invention has been made in consideration of the above-mentioned circumstances, and an object of the invention is to provide an endoscope apparatus and a method of operating the endoscope apparatus that perform both illumination light observation and fluorescence observation by a simple configuration.

To achieve the object of the invention, there is provided an endoscope apparatus performing illumination light observation that irradiates a portion to be observed with illumination light and observes the portion to be observed and fluorescence observation that irradiates the portion to be observed with excitation light to allow a fluorescent material, which is contained in the portion to be observed, to be excited to emit light and observes fluorescence. The endoscope apparatus comprises: a light irradiation section that irradiates the portion to be observed with the illumination light and the excitation light while switching the illumination light and the excitation light; an image pickup unit that picks up an image using reflected light of the illumination light reflected from the portion to be observed and outputs a reflected light-image pickup signal in a case in which the portion to be observed is irradiated with the illumination light from the light irradiation section, and picks up an image using the fluorescence and outputs a fluorescence-image pickup signal in a case in which the portion to be observed is irradiated with the excitation light from the light irradiation section; and color filters that are provided in the image pickup unit, transmit the illumination light and the excitation light, and include a first color filter having a first spectral transmittance characteristic and a second color filter having a second spectral transmittance characteristic of which a peak of transmittance is closer to a long wavelength side than a peak of transmittance of the first spectral transmittance characteristic. In a case in which a peak value of absorption intensity of the fluorescent material is referred to as a first peak value and a wavelength region where the absorption intensity of the fluorescent material is 10% or more of the first peak value is referred to as a first wavelength region, at least a part of a wavelength region of the excitation light is included in the first wavelength region. In a case in which a peak value of transmittance of the first spectral transmittance characteristic is referred to as a second peak value, a peak value of transmittance of the second spectral transmittance characteristic is referred to as a third peak value, a wavelength region where the transmittance of the first spectral transmittance characteristic is 60% or more of the second peak value is referred to as a second wavelength region, and a wavelength region where the transmittance of the second spectral transmittance characteristic is 40% or less of the third peak value is referred to as a third wavelength region, the wavelength region of the excitation light is included in the second wavelength region and the third wavelength region. In a case in which a wavelength region where the transmittance of the second spectral transmittance characteristic is 80% or more of the third peak value is referred to as a fourth wavelength region, a wavelength at which intensity of the fluorescence is a peak (maximum) is included in the fourth wavelength region. Here, the peak value of the absorption intensity of the fluorescent material is the peak value (maximum value) of absorption intensity in the entire wavelength region, and the peak value of the transmittance of each spectral transmittance characteristic is the peak value (maximum value) of the transmittance in the entire wavelength region.

According to this endoscope apparatus, a good fluorescence image is obtained by a simple configuration without the disposition of a filter for fluorescence observation, a filter for reducing the intensity of excitation light, or the like in the tip portion of the endoscope.

According to another aspect of the invention, in the endoscope apparatus, the first wavelength region is a wavelength region where the absorption intensity of the fluorescent material is 50% or more of the first peak value. Accordingly, since "fluorescence emission intensity" representing the intensity of fluorescence emitted from the fluorescent material is sufficiently increased, a good fluorescence image is obtained.

According to another aspect of the invention, in the endoscope apparatus, the first wavelength region is included in a wavelength region of blue light, and the fluorescence is green fluorescence. Accordingly, since color separation between the excitation light and the fluorescence detected by the image pickup unit is good, a good fluorescence image is obtained.

According to another aspect of the invention, in the endoscope apparatus, the excitation light is blue light. Accordingly, since color separation between the excitation light and the fluorescence detected by the image pickup unit is good, a good fluorescence image is obtained.

According to another aspect of the invention, in the endoscope apparatus, a wavelength region of the first spectral transmittance characteristic and a wavelength region of the second spectral transmittance characteristic partially overlap each other. According to the endoscope apparatus, a good fluorescence image is obtained even in this case.

According to another aspect of the invention, in the endoscope apparatus, the second wavelength region is a wavelength region where the transmittance of the first spectral transmittance characteristic is 80% or more of the second peak value. Accordingly, since the excitation light and the fluorescence are separated from each other and color separation between the excitation light and the fluorescence detected by the image pickup element is good, a good fluorescence image is obtained.

According to another aspect of the invention, in the endoscope apparatus, the third wavelength region is a wavelength region where the transmittance of the second spectral transmittance characteristic is 20% or less of the third peak value. Accordingly, since the excitation light and the fluorescence are separated from each other and color separation between the excitation light and the fluorescence detected by the image pickup element is good, a good fluorescence image is obtained.

According to another aspect of the invention, in the endoscope apparatus, the light irradiation section includes three or more types semiconductor light sources emitting three or more types of the excitation light that are included in a wavelength region corresponding to a bluish color including purple and blue and have peak wavelengths of light intensity different from each other. Accordingly, narrow-band light observation using narrow-band light can be performed as the illumination light observation in addition to the normal observation using white light, and the observation of an oxygen saturation image (oxygen saturation observation) can also be performed.

According to another aspect of the invention, in the endoscope apparatus, the semiconductor light source includes a first semiconductor light source that emits purple light, a second semiconductor light source that emits first blue light of a short wavelength-side wavelength region obtained in a case in which a wavelength region corresponding to a wavelength longer than a predetermined wavelength is cut out of a wavelength region of blue light, and a third semiconductor light source that emits second blue light of a long wavelength-side wavelength region obtained in a case in which a wavelength region corresponding to a wavelength shorter than the predetermined wavelength is cut out of the wavelength region of the blue light, and the light irradiation section emits the purple light, which is emitted from the first semiconductor light source, and the first blue light, which is emitted from the second semiconductor light source, as the illumination light and emits the first blue light, which is emitted from the second semiconductor light source, and the second blue light, which is emitted from the third semiconductor light source, as the excitation light. Accordingly, narrow-band light observation using narrow-band light can be performed as the illumination light observation in addition to the normal observation using white light, and the observation of an oxygen saturation image (oxygen saturation observation) can also be performed.

According to another aspect of the invention, in the endoscope apparatus, the illumination light is white light, the light irradiation section has a special emission mode in which the white light including the second blue light and the second blue light are emitted to the portion to be observed while being switched, and the image pickup unit picks up an image using reflected light of the white light and outputs the reflected light-image pickup signal and picks up an image using reflected light of the second blue light and outputs a blue reflected light-image pickup signal in a case in which the light irradiation section is in the special emission mode. The endoscope apparatus further comprises an oxygen saturation image generating unit that generates an oxygen saturation image representing oxygen saturation of the portion to be observed on the basis of the reflected light-image pickup signal and the blue reflected light-image pickup signal output from the image pickup unit. Accordingly, the observation of an oxygen saturation image (oxygen saturation observation) can also be simultaneously performed in addition to the illumination light observation and the fluorescence observation.

According to another aspect of the invention, in the endoscope apparatus, the semiconductor light source is a light emitting diode.

According to another aspect of the invention, in a case in which the excitation light is blue light and the fluorescence is red fluorescence in the endoscope apparatus, a wavelength region of the first spectral transmittance characteristic and a wavelength region of the second spectral transmittance characteristic are separated from each other. Accordingly, since the excitation light and the fluorescence are separated from each other and color separation between the excitation light and the fluorescence detected by the image pickup element is good, a good fluorescence image is obtained.

According to another aspect of the invention, in the endoscope apparatus, the first color filter and the second color filter are primary color filters.

According to another aspect of the invention, the endoscope apparatus further comprises a fluorescence image generating unit that generates a fluorescence image of the portion to be observed on the basis of the reflected light-image pickup signal and the fluorescence-image pickup signal output from the image pickup unit.

According to another aspect of the invention, in the endoscope apparatus, the image pickup unit includes an image pickup element that includes a plurality of two-dimensionally arranged pixels and the color filters. The endoscope apparatus further comprises: a drive control unit for the image pickup element that makes a time, in which electrical charges are accumulated in the pixels of the image pickup element in a case where the portion to be observed is irradiated with the excitation light from the light irradiation section, be longer than a time in which electrical charges are accumulated in the pixels of the image pickup element in a case where the portion to be observed is irradiated with the illumination light from the light irradiation section. Accordingly, a difference in intensity between the reflected light-image pickup signal and the fluorescence-image pickup signal can be compensated.

To achieve the object of the invention, there is provided a method of operating an endoscope apparatus. The endoscope apparatus comprises a light irradiation section that selectively irradiates a portion to be observed with illumination light and excitation light, and an image pickup unit that includes color filters includes a first color filter having a first spectral transmittance characteristic and a second color filter having a second spectral transmittance characteristic of which a peak of transmittance is closer to a long wavelength side than a peak of transmittance of the first spectral transmittance characteristic. The endoscope apparatus performs illumination light observation that irradiates the portion to be observed with the illumination light from the light irradiation section and observes the portion to be observed, and fluorescence observation that irradiates the portion to be observed with the excitation light from the light irradiation section to allow a fluorescent material, which is contained in the portion to be observed, to be excited to emit light and observes fluorescence. The light irradiation section irradiates the portion to be observed with the illumination light and the excitation light while switching the illumination light and the excitation light. The image pickup unit picks up an image using reflected light of the illumination light reflected from the portion to be observed and outputs a reflected light-image pickup signal in a case in which the portion to be observed is irradiated with the illumination light from the light irradiation section, and picks up an image using the fluorescence and outputs a fluorescence-image pickup signal in a case in which the portion to be observed is irradiated with the excitation light from the light irradiation section. In a case in which a peak value of absorption intensity of the fluorescent material is referred to as a first peak value and a wavelength region where the absorption intensity of the fluorescent material is 10% or more of the first peak value is referred to as a first wavelength region, at least a part of a wavelength region of the excitation light is included in the first wavelength region. In a case in which a peak value of transmittance of the first spectral transmittance characteristic is referred to as a second peak value, a peak value of transmittance of the second spectral transmittance characteristic is referred to as a third peak value, a wavelength region where the transmittance of the first spectral transmittance characteristic is 60% or more of the second peak value is referred to as a second wavelength region, and a wavelength region where the transmittance of the second spectral transmittance characteristic is 40% or less of the third peak value is referred to as a third wavelength region, the wavelength region of the excitation light is included in the second wavelength region and the third wavelength region. In a case in which a wavelength region where the transmittance of the second spectral transmittance characteristic is 80% or more of the third peak value is referred to as a fourth wavelength region, a wavelength at which intensity of the fluorescence is a peak is included in the fourth wavelength region.

An endoscope apparatus and a method of operating the endoscope apparatus of the invention can perform both illumination light observation and fluorescence observation by a simple configuration.

BRIEF DESCRIPTION OF THE DRAWINGS

FIG. 29 is a diagram illustrating conditions and evaluation results of Examples 1 to 11.

FIG. 30 is a diagram illustrating conditions and evaluation results of Examples 12 to 27.

DESCRIPTION OF THE PREFERRED EMBODIMENTS

Entire Configuration of Endoscope Apparatus of First Embodiment

Figure 1:
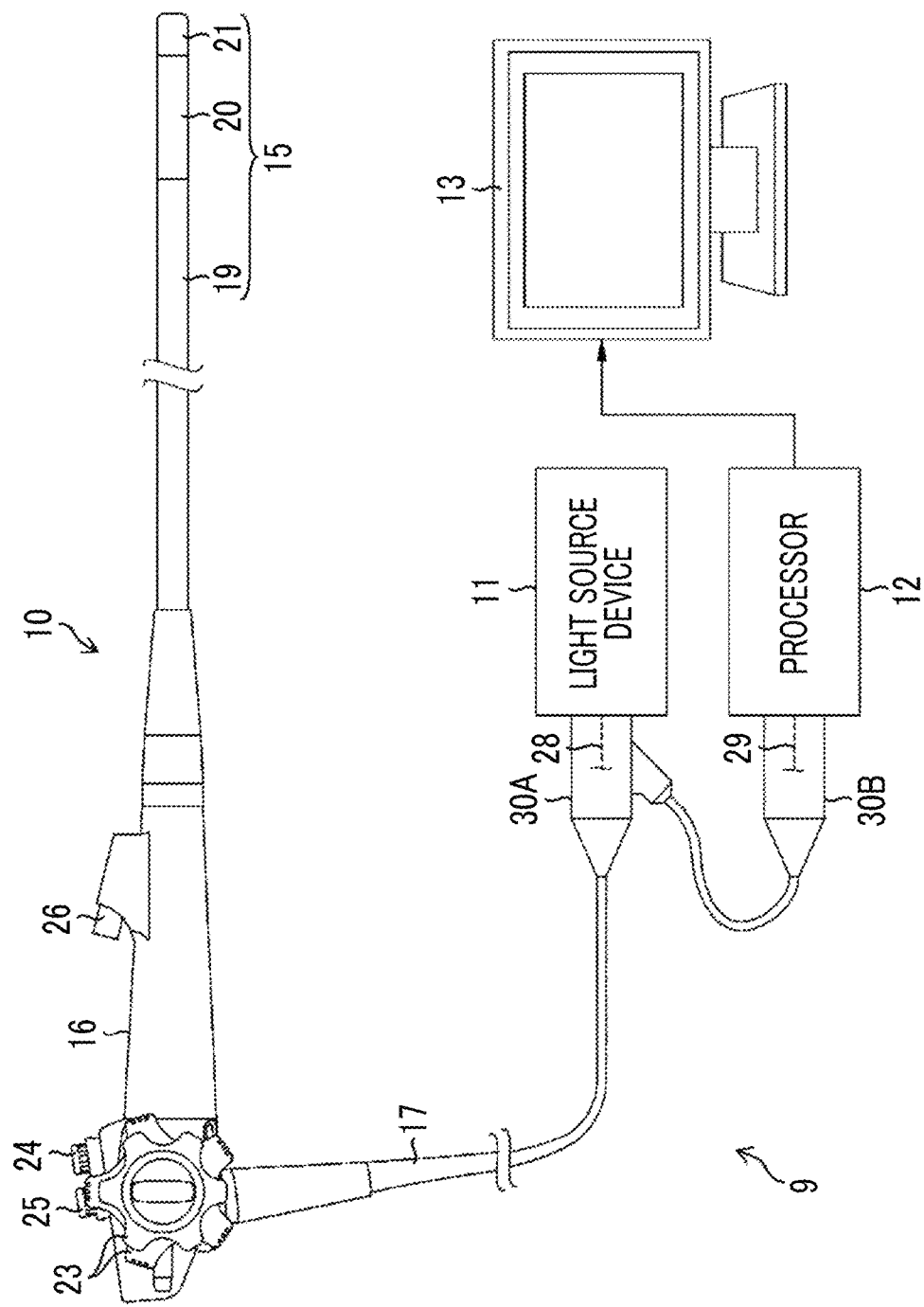
FIG. 1 is a schematic diagram showing the entire configuration of an endoscope apparatus of a first embodiment.

FIG. 1 is a schematic diagram showing the entire configuration of an endoscope apparatus 9 (referred to as an endoscope system) of a first embodiment. As shown in FIG. 1, the endoscope apparatus 9 includes an electronic endoscope 10 (hereinafter, simply abbreviated as an endoscope 10), a light source device 11, a processor 12, and a monitor 13.

For example, a flexible endoscope is used as the endoscope 10 in this embodiment. The endoscope 10 includes an insertion part 15 that is to be inserted into a subject and includes a tip and a base end, an operation unit 16 that is connected to a base end side of the insertion part 15 and allows an operator to perform various operations in a state in which the operator grips the operation unit 16, and a universal cord 17 that is connected to the operation unit 16.

The insertion part 15 is formed to have a small diameter and a long shape as a whole. The insertion part 15 includes a soft portion 19, a bendable portion 20, and a tip portion 21 that are arranged in this order from the base end side toward a tip side and are connected to each other. The soft portion 19 has flexibility, the bendable portion 20 can be bent by the operation of the operation unit 16, and an image pickup element 49 (see FIG. 2) to be described later and the like are built in the tip portion 21.

The operation unit 16 is provided with various operation members that are to be operated by an operator. Specifically, the operation unit 16 is provided with two types of bending operation knobs 23 that are used for a lateral bending operation and a vertical bending operation of the bendable portion 20, an air/water supply button 24 for an air/water supply operation, and a suction button 25 for a suction operation. Further, the operation unit 16 is provided with a treatment tool inlet 26 through which a treatment tool is inserted into a treatment tool insertion passage (not shown) inserted into the insertion part 15.

The universal cord 17 is a connecting cord that is used to connect the endoscope 10 to the light source device 11. The universal cord 17 includes a light guide 28, a signal cable 29, and a fluid tube (not shown) that are inserted into the insertion part 15. Furthermore, a connector 30A that is to be connected to the light source device 11 and a connector 30B that is branched from the connector 30A and is to be connected to the processor 12 are provided at an end portion of the universal cord 17.

In a case in which the connector 30A is connected to the light source device 11, the light guide 28 and the fluid tube (not shown) are inserted into the light source device 11. Accordingly, necessary light, water, and gas are supplied to the endoscope 10 from the light source device 11 through the light guide 28 and the fluid tube (not shown). Further, in a case in which the connector 30B is connected to the processor 12, the signal cable 29 and the processor 12 are electrically connected to each other. Accordingly, an image pickup signal of a portion 34 to be observed (see FIG. 2) is output to the processor 12 from the endoscope 10 and a control signal is output to the endoscope 10 from the processor 12 through the signal cable 29.

The light source device 11 selectively supplies illumination light for normal observation (white light W, see FIG. 2) and excitation light EL for fluorescence observation (see FIG. 2), which will be described later, to the light guide 28 of the endoscope 10 through the connector 30A. The processor 12 controls the operation of the endoscope 10 and outputs an image, which is based on the image pickup signal acquired from the endoscope 10, to the monitor 13 through the connector 30B and the signal cable 29. The monitor 13 displays the image input from the processor 12.

Internal Configuration of Endoscope Apparatus of First Embodiment

Figure 2:
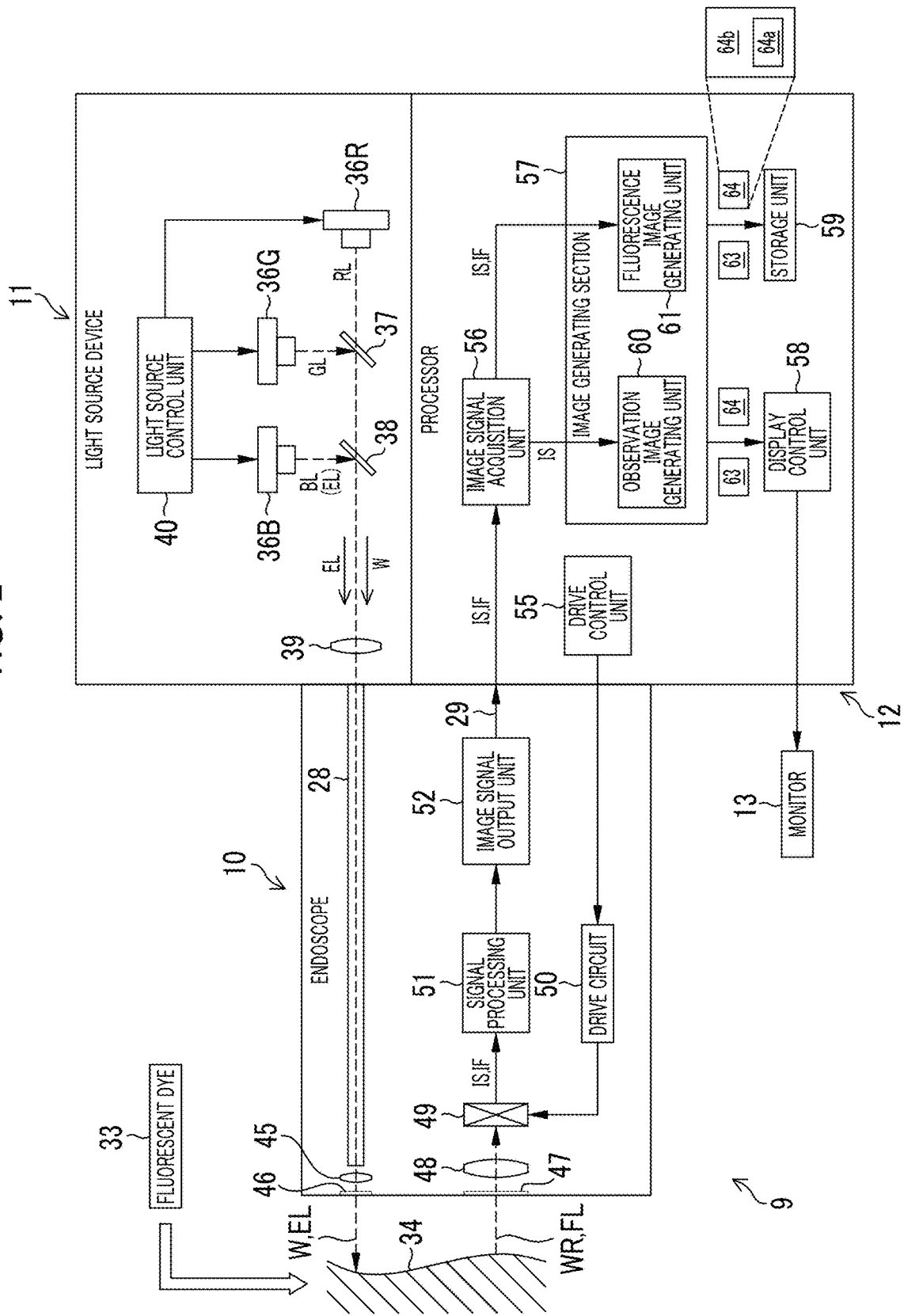
FIG. 2 is a schematic diagram of the internal configuration of the endoscope apparatus of the first embodiment.

FIG. 2 is a schematic diagram of the internal configuration of the endoscope apparatus 9 of the first embodiment. As shown in FIG. 2, the endoscope apparatus 9 performs both the fluorescence observation for the portion 34 to be observed to which a fluorescent dye 33 corresponding to a fluorescent material of the invention is applied, that is, the portion 34 to be observed labeled by a fluorescent dye 33 and the normal observation (corresponding to illumination light observation of the invention) for the portion 34 to be observed.

Here, the fluorescence observation is to irradiate the portion 34 to be observed with the excitation light EL to allow the fluorescent dye 33, which is contained in the portion 34 to be observed, to be excited to emit light and to observe the portion 34 to be observed on the basis of an image that is obtained from the image pickup using the emitted fluorescence FL. Further, the normal observation is to irradiate the portion 34 to be observed with white light W (corresponding to the illumination light of the invention) and to observe the portion 34 to be observed on the basis of an image that is obtained from the image pickup using reflected light WR reflected from the portion 34 to be observed.

Fluorescein, more specifically, fluorescein isothiocyanate (FITC) is used as the fluorescent dye 33 in this embodiment. In a case in which the fluorescent dye 33 is irradiated with excitation light EL (blue light BL) included in a blue wavelength region (wavelength band), the fluorescent dye 33 is excited to emit light and emits fluorescence FL that is green fluorescence included in a green wavelength region (wavelength band) (see FIG. 7). Hereinafter, fluorescein isothiocyanate will be also simply referred to as "fluorescein".

Light Source Device

The light source device 11 forms a light irradiation section of the invention together with the light guide 28 of the endoscope 10 and an irradiation lens 45 and an illumination window 46 to be described later. The light source device 11 includes a semiconductor light source 36R, a semiconductor light source 36G, a semiconductor light source 36B, a dichroic filter 37, a dichroic filter 38, a lens 39, and a light source control unit 40.

For example, a light emitting diode (LED) is used as each of the semiconductor light sources 36R, 36G, and 36B. Various light sources, such as a laser diode (LD) and a halogen lamp, may be used instead of the light emitting diode.

Figure 3:
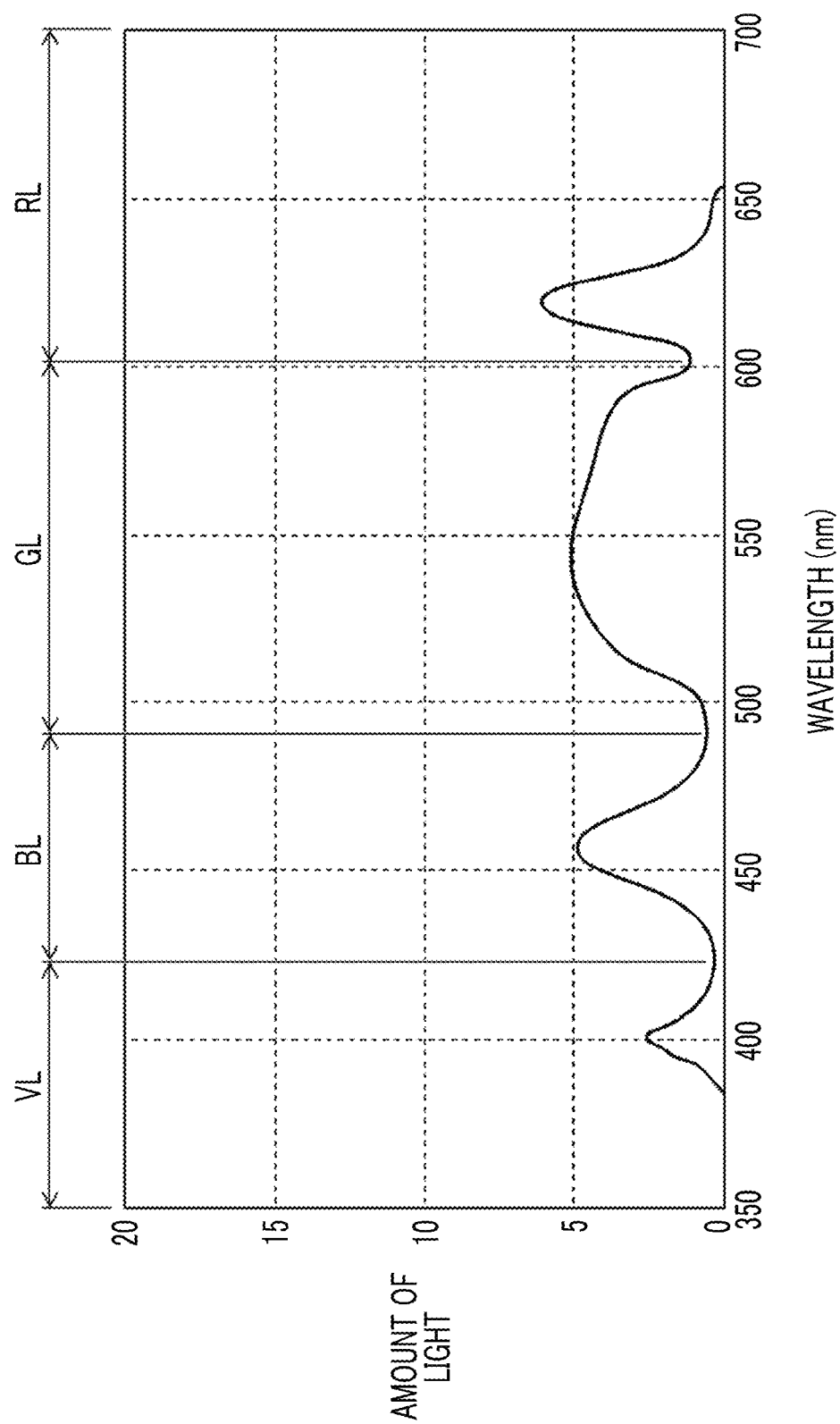
FIG. 3 is a graph showing an example of the spectral characteristics of respective color lights emitted from respective semiconductor light sources of a light source device.

FIG. 3 is a graph showing an example of the spectral characteristics of the respective color lights emitted from the respective semiconductor light sources 36R, 36G, and 36B of the light source device 11. As shown in FIG. 3, the semiconductor light source 36R emits red light RL that is light of a red wavelength region. The semiconductor light source 36G emits green light GL that is light of a green wavelength region. The semiconductor light source 36B emits blue light BL that is light of a blue wavelength region. Although described in detail later, purple light VL shown in FIG. 3 is light of a purple wavelength region and is light to be used as the above-mentioned excitation light EL together with blue light BL or instead of blue light BL. The wavelength region of each color light is not limited to the wavelength region shown in FIG. 3 and may be appropriately changed.

Returning to FIG. 2, the optical path of red light RL emitted from the semiconductor light source 36R is orthogonal to the optical path of green light GL emitted from the semiconductor light source 36G and the optical path of blue light BL emitted from the semiconductor light source 36B. The semiconductor light sources 36G and 36B emit green light GL and blue light BL toward the optical path of red light RL, respectively.

The dichroic filter 37 is disposed at an intersection between the optical path of red light RL and the optical path of green light GL. The dichroic filter 37 transmits red light RL incident from the semiconductor light source 36R, and reflects green light GL, which is incident from the semiconductor light source 36G, to the dichroic filter 38. Accordingly, red light RL and green light GL can be incident on the dichroic filter 38.

The dichroic filter 38 is disposed at an intersection between the optical path of red light RL and the optical path of blue light BL. The dichroic filter 38 transmits red light RL and green light GL incident from the dichroic filter 37, and reflects blue light BL, which is incident from the semiconductor light source 36B, to the lens 39. Accordingly, in a case in which all the respective semiconductor light sources 36R, 36G, and 36B are operated, white light W including red light RL, green light GL, and blue light BL can be incident on the lens 39. Further, although described in detail later, blue light BL (excitation light EL) can be incident on the lens 39 in a case in which only the semiconductor light source 36B is operated.

White light W, which is mentioned in this specification, is not limited to light exactly including all wavelength components of visible light. For example, white light W may be light including light of specific wavelength regions, such as red light RL, green light GL, and blue light BL, and may also be light further including light of a wavelength region over red from green, light of a wavelength region over green from blue, or the like in a broad sense.

The lens 39 makes white light W or blue light BL, which is incident from the dichroic filter 38, be incident on the light guide 28 of the endoscope 10 through the connector 30A.

The light source control unit 40 controls the operation of each of the semiconductor light sources 36R, 36G, and 36B. In a case in which the normal observation is performed, the light source control unit 40 simultaneously operates the respective semiconductor light sources 36R, 36G, and 36B to make white light W be emitted from the light source device 11 as illumination light and makes the white light W be incident on the light guide 28 of the endoscope 10. Further, in a case in which the fluorescence observation is performed, the light source control unit 40 operates only the semiconductor light source 36B to make blue light BL be emitted from the light source device 11 as excitation light EL and makes the excitation light EL be incident on the light guide 28 of the endoscope 10.

Since the normal observation and the fluorescence observation are performed simultaneously (in parallel) in this embodiment, the light source control unit 40 alternately switches the emission of white light W and the emission of excitation light EL at regular time intervals or by the imaging frame of the image pickup element 49 to be described later (see FIGS. 5 and 6). Accordingly, a so-called multi-frame function to simultaneously or sequentially update, display and record an image of the normal observation and an image of the fluorescence observation on the monitor 13 is realized.

Endoscope

The endoscope 10 includes the light guide 28, an irradiation lens 45, an illumination window 46, an observation window 47, a condenser lens 48, the image pickup element 49, a drive circuit 50, a signal processing unit 51, an image signal output unit 52, the signal cable 29, the fluid tube (not shown), and an air/water supply nozzle.

The light guide 28 is large-diameter optical fiber or bundled fiber. An incident end of the light guide 28 is connected to the light source device 11 through the connector 30A. The light guide 28 passes through the inside of each of the connector 30A, the universal cord 17, the operation unit 16, and the insertion part 15, and an emitting end of the light guide 28 faces the irradiation lens 45 provided in the tip portion 21 of the insertion part 15. Accordingly, white light W or excitation light EL, which is supplied to the incident end of the light guide 28 from the light source device 11, is applied to the portion 34 to be observed from the irradiation lens 45 through the illumination window 46 that is provided on the tip surface of the tip portion 21.

In a case in which the portion 34 to be observed is irradiated with white light W, reflected light WR of the white light W reflected from the portion 34 to be observed is incident on the observation window 47, which is provided on the tip surface of the tip portion 21, as the image light of the portion 34 to be observed. Further, in a case in which the portion 34 to be observed is irradiated with excitation light EL, the fluorescent dye 33 contained in the portion 34 to be observed is excited by the excitation light EL so as to emit light and fluorescence FL emitted from the fluorescent dye 33 is incident on the observation window 47.

The condenser lens 48 makes reflected light WR and fluorescence FL, which are incident through the observation window 47, be incident on an image pickup surface of the image pickup element 49.

The image pickup element 49 forms an image pickup unit of the invention together with the already-described condenser lens 48, and is a complementary metal oxide semiconductor (CMOS) type or charge coupled device (CCD) type color image pickup element (referred to as a color image sensor). In a case in which reflected light WR is incident on the image pickup surface of the image pickup element 49, the image pickup element 49 picks up an image using the reflected light WR, that is, converts the reflected light WR into an electrical signal and outputs a reflected light-image pickup signal IS, which is an image pickup signal of the reflected light WR, to the signal processing unit 51. Further, in a case in which fluorescence FL is incident on the image pickup surface of the image pickup element 49, the image pickup element 49 picks up an image using the fluorescence FL and outputs a fluorescence-image pickup signal IF, which is an image pickup signal of the fluorescence FL, to the signal processing unit 51. Since the light source device 11 alternately emits white light W and excitation light EL as already described, the image pickup element 49 alternately outputs the reflected light-image pickup signals IS and the fluorescence-image pickup signals IF in accordance with the alternate emission of the white light W and the excitation light EL.

It is preferable that the image pickup of the image pickup element 49 and the switching of emission of white light W and excitation light EL from the light source device 11 are performed at a timing synchronized with a synchronization signal (not shown) (also referred to as a reference signal).

Figure 4:
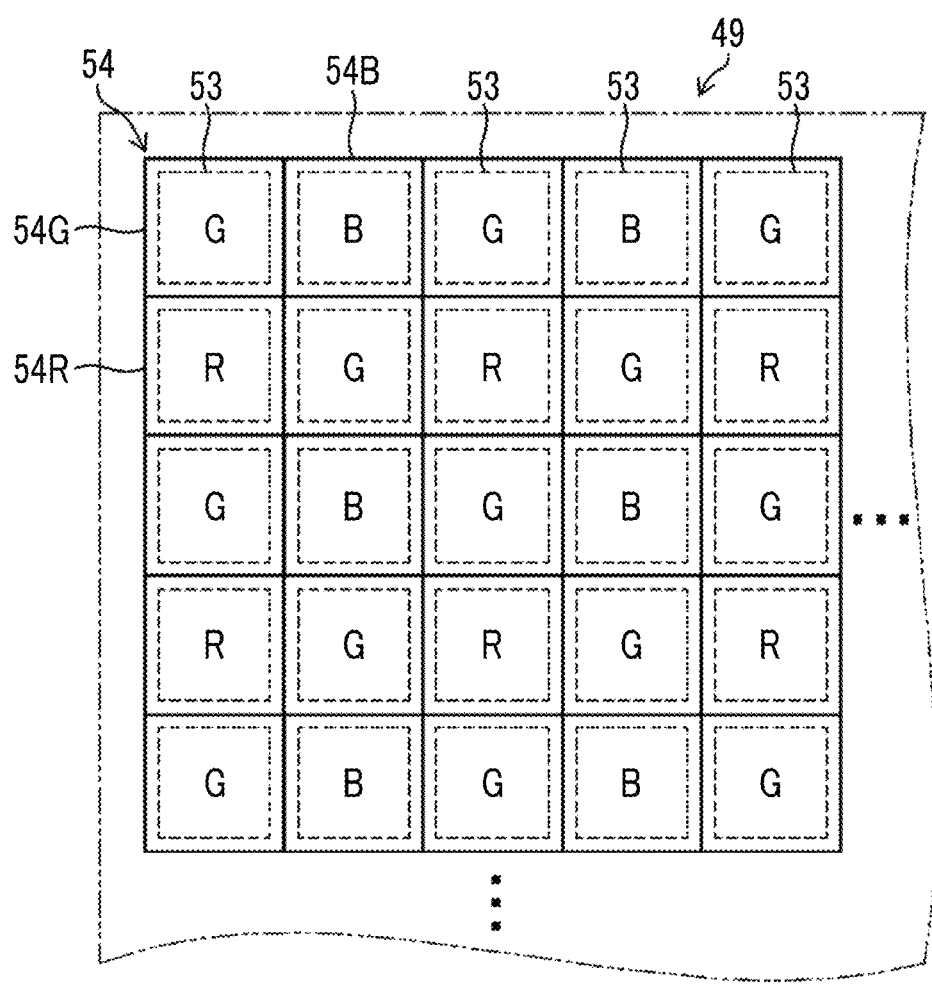
FIG. 4 is a front view of an image pickup surface of an image pickup element.

FIG. 4 is a front view of the image pickup surface of the image pickup element 49. As shown in FIG. 4, a plurality of pixels 53 (photoelectric conversion elements) are two-dimensionally arranged on the image pickup surface of the image pickup element 49. Further, color filters 54 having a red (R) color, a green (G) color, and a blue (B) color are disposed on the respective pixels 53. A light-shielding film, a microlens, and the like are not shown to prevent the complication of the drawings.

The color filters 54 include red (R) color filters 54R, green (G) color filters 54G, and blue (B) color filters 54B. The color filters 54R, 54G, and 54B having the respective colors are primary color filters of the invention, and arranged on the respective pixels 53 at, for example, a publicly-known Bayer array pattern, but other publicly-known array patterns may be employed. In this embodiment, the color filter 54B corresponds to a first color filter of the invention and the color filter 54G corresponds to a second color filter of the invention.

Returning to FIG. 2, the drive circuit 50 controls the drive of the image pickup element 49 under the control of a drive control unit 55 of the processor 12 to be described later.

The signal processing unit 51 performs various types of signal processing on the reflected light-image pickup signals IS and the fluorescence-image pickup signals IF that are alternately output from the image pickup element 49, and outputs the signals to the image signal output unit 52. The image signal output unit 52 outputs the reflected light-image pickup signals IS and the fluorescence-image pickup signals IF, which are input from the signal processing unit 51 and have been subjected to the signal processing, to the processor 12 through the connector 30B (see FIG. 1) and the signal cable 29.

Processor

The processor 12 includes the drive control unit 55, an image signal acquisition unit 56, an image generating section 57, a display control unit 58, and a storage unit 59.

The drive control unit 55 is electrically connected to the drive circuit 50 of the endoscope 10 through the connector 30B and a signal line (not shown). The drive control unit 55 controls the drive of the image pickup element 49 through the drive circuit 50.

Here, since the intensity of fluorescence FL is lower than the intensity of the reflected light WR, the intensity of the fluorescence-image pickup signal IF is lower than the intensity of the reflected light-image pickup signal IS. Further, the drive control unit 55 compensates a difference in intensity between the reflected light-image pickup signal IS and the fluorescence-image pickup signal IF by making a time in which electrical charges are accumulated in the respective pixels 53 of the image pickup element 49 during the fluorescence observation be longer than a time in which electrical charges are accumulated in the respective pixels 53 during the normal observation through the drive circuit 50.

Figure 5:
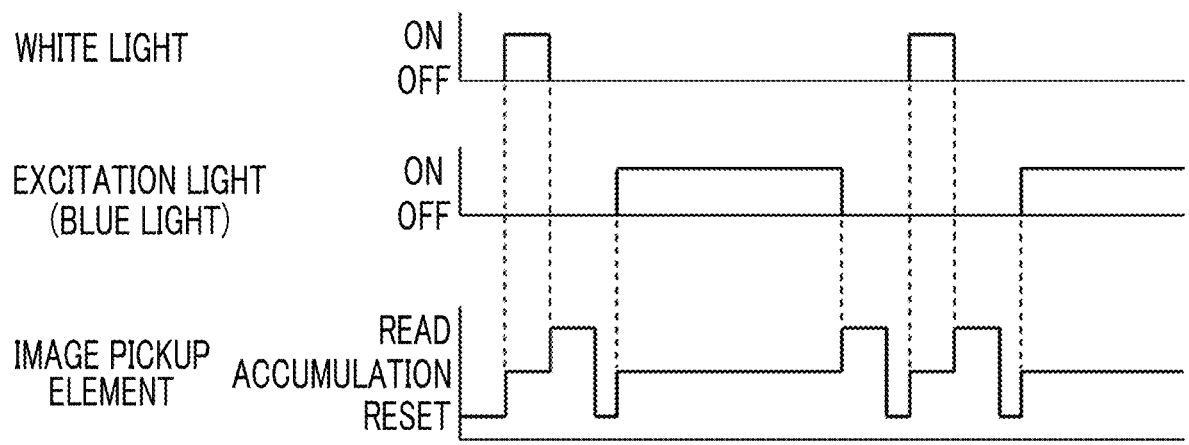
FIG. 5 is a diagram illustrating an example of the drive control of the image pickup element that is performed by a drive control unit to compensate a difference in intensity between a reflected light-image pickup signal and a fluorescence-image pickup signal.

FIG. 5 is a diagram illustrating an example of the drive control of the image pickup element 49 that is performed by the drive control unit 55 to compensate a difference in intensity between the reflected light-image pickup signal IS and the fluorescence-image pickup signal IF. Further, FIG. 6 is a diagram illustrating another example of the drive control of the image pickup element 49 that is performed by the drive control unit 55 to compensate a difference in intensity between the reflected light-image pickup signal IS and the fluorescence-image pickup signal IF.

As shown in FIG. 5, the drive control unit 55 controls the drive of the image pickup element 49 so that the shutter speed of the image pickup element 49 in a case in which excitation light EL is applied during the fluorescence observation is lower than the shutter speed of the image pickup element 49 in a case in which white light W is applied during the normal observation. Accordingly, a time in which electrical charges are accumulated in the pixels 53 in a case in which excitation light EL is applied is longer than that in a case in which white light W is applied. For this reason, sufficient electrical charges are accumulated in the pixels 53 even in the case of the fluorescence FL of which the intensity is lower than the intensity of the reflected light WR of the white light W. Accordingly, a difference in intensity between the reflected light-image pickup signal IS and the fluorescence-image pickup signal IF is compensated.

Figure 6:
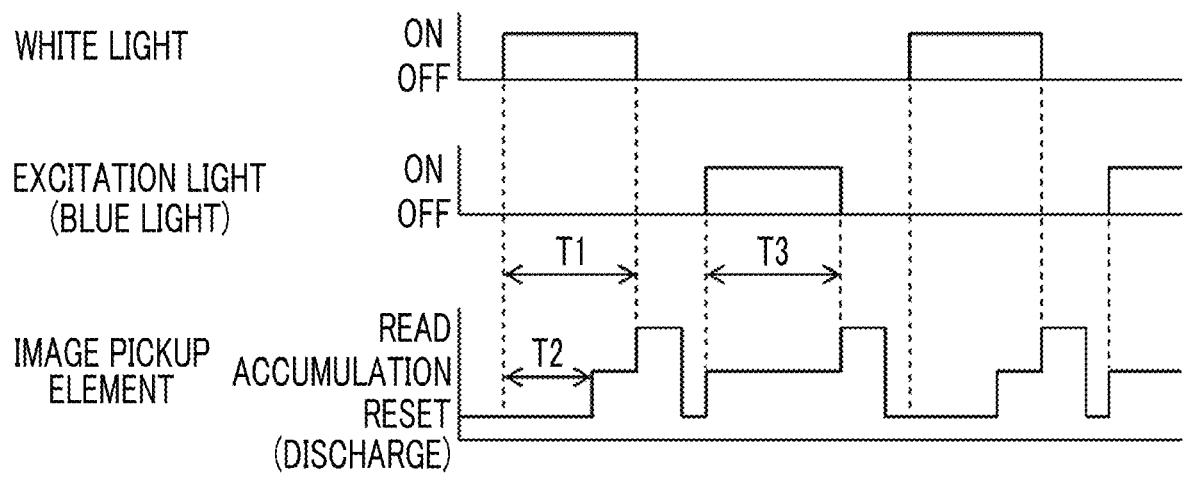
FIG. 6 is a diagram illustrating another example of the drive control of the image pickup element that is performed by the drive control unit to compensate a difference in intensity between a reflected light-image pickup signal and a fluorescence-image pickup signal.

Further, as shown in FIG. 6, the drive control unit 55 controls the drive of the image pickup element 49 so that electrical charges, which are generated by each pixel 53 of the image pickup element 49 in a period T1 where white light W for the normal observation is applied, are discharged only in a predetermined period T2 shorter than the period T1. On the other hand, the drive control unit 55 controls the drive of the image pickup element 49 so that electrical charges are not discharged in a period T3 (T3=T1) where excitation light EL for the fluorescence observation is applied and are accumulated in the pixels 53 over the entire period T3. Accordingly, as in the example that has been described in already-described FIG. 5, a time in which electrical charges are accumulated in the pixels 53 in a case in which excitation light EL is applied is longer than that in a case in which white light W is applied. As a result, a difference in intensity between the reflected light-image pickup signal IS and the fluorescence-image pickup signal IF is compensated.

Returning to FIG. 2, the image signal acquisition unit 56 acquires the reflected light-image pickup signals IS and the fluorescence-image pickup signals IF, which are alternately and sequentially output from the image signal output unit 52, through the signal cable 29 and the connector 30B and sequentially outputs the reflected light-image pickup signals IS and the fluorescence-image pickup signals IF to the image generating section 57.

The image generating section 57 functions as an observation image generating unit 60 and a fluorescence image generating unit 61. The observation image generating unit 60 sequentially acquires the reflected light-image pickup signals IS from the image signal acquisition unit 56, and generates an observation image 63, which is a white light image of the portion 34 to be observed, on the basis of a new reflected light-image pickup signal IS whenever acquiring the new reflected light-image pickup signal IS. Further, the observation image generating unit 60 sequentially outputs the generated observation image 63 to the display control unit 58 and the storage unit 59.

Whenever acquiring a new reflected light-image pickup signal IS and a new fluorescence-image pickup signal IF from the image signal acquisition unit 56, the fluorescence image generating unit 61 generates a fluorescence image 64 on the basis of the new reflected light-image pickup signal IS and the new fluorescence-image pickup signal IF. Specifically, the fluorescence image generating unit 61 generates a simple fluorescence image 64a on the basis of the newly acquired fluorescence-image pickup signal IF, generates a background image 64b on the basis of the reflected light-image pickup signal IS, and combines the simple fluorescence image 64a with the background image 64b to generate a fluorescence image 64. Further, the fluorescence image generating unit 61 sequentially outputs the generated fluorescence image 64 to the display control unit 58 and the storage unit 59.

The observation image 63, which is generated by the observation image generating unit 60, may be used as the above-mentioned background image 64b. Further, in a case in which the background image 64b is unnecessary for the fluorescence image 64, the fluorescence image generating unit 61 generates a fluorescence image 64, which is equivalent to the above-mentioned simple fluorescence image 64a, on the basis of only the fluorescence-image pickup signal IF that is newly acquired from the image signal acquisition unit 56.

The display control unit 58 sequentially outputs the observation image 63 and the fluorescence image 64, which are sequentially input from the observation image generating unit 60 and the fluorescence image generating unit 61, to the monitor 13, to make the monitor 13 display the observation image 63 and the fluorescence image 64 in the form of a moving image (for example, make simultaneously display or alternately display the observation image 63 and the fluorescence image 64). Further, the storage unit 59 sequentially stores the observation image 63 and the fluorescence image 64 that are sequentially input from the observation image generating unit 60 and the fluorescence image generating unit 61. Accordingly, the above-mentioned multi-frame function is realized.

Conditions Required to Obtain Good Fluorescence Image

Next, conditions where a good fluorescence image 64 is obtained in the endoscope apparatus 9 having the above-mentioned configuration will be described. The endoscope apparatus 9 of this embodiment satisfies a criterion [A] and a criterion [B] to be described below to obtain a good fluorescence image 64 while simultaneously performing the normal observation and the fluorescence observation.

The criterion [A] means that "sensor color separation" is good. "Sensor color separation" represents that excitation light EL and fluorescence FL are separately detected by the image pickup element 49, that is, excitation light EL is detected by only the blue pixel 53 and fluorescence FL is detected by only the green pixel 53. Since excitation light EL and fluorescence FL are simultaneously detected by, for example, the green pixel 53 of the image pickup element 49 in a case in which "sensor color separation" is poor, a good simple fluorescence image 64a cannot be generated. As a result, a good fluorescence image 64 is not obtained.

The criterion [B] means that "fluorescence emission intensity" representing the intensity of fluorescence FL emitted from the fluorescent dye 33 is sufficiently high. Since a simple fluorescence image 64a is dark in a case in which "fluorescence emission intensity" is low, a good fluorescence image 64 is not obtained. In this embodiment, as described in already-described FIGS. 5 and 6, a difference in intensity between the reflected light-image pickup signal IS and the fluorescence-image pickup signal IF is compensated by the drive control unit 55. However, in a case in which "fluorescence emission intensity" is sufficiently high, control performed by the drive control unit 55 can be omitted or a time in which electrical charges are accumulated during the fluorescence observation can be shortened.

Among a condition for satisfying the criterion [A] and a condition for satisfying the criterion [B], the condition for satisfying the criterion [B] will be described first.

Condition for Satisfying Criterion [B]

Figure 7:
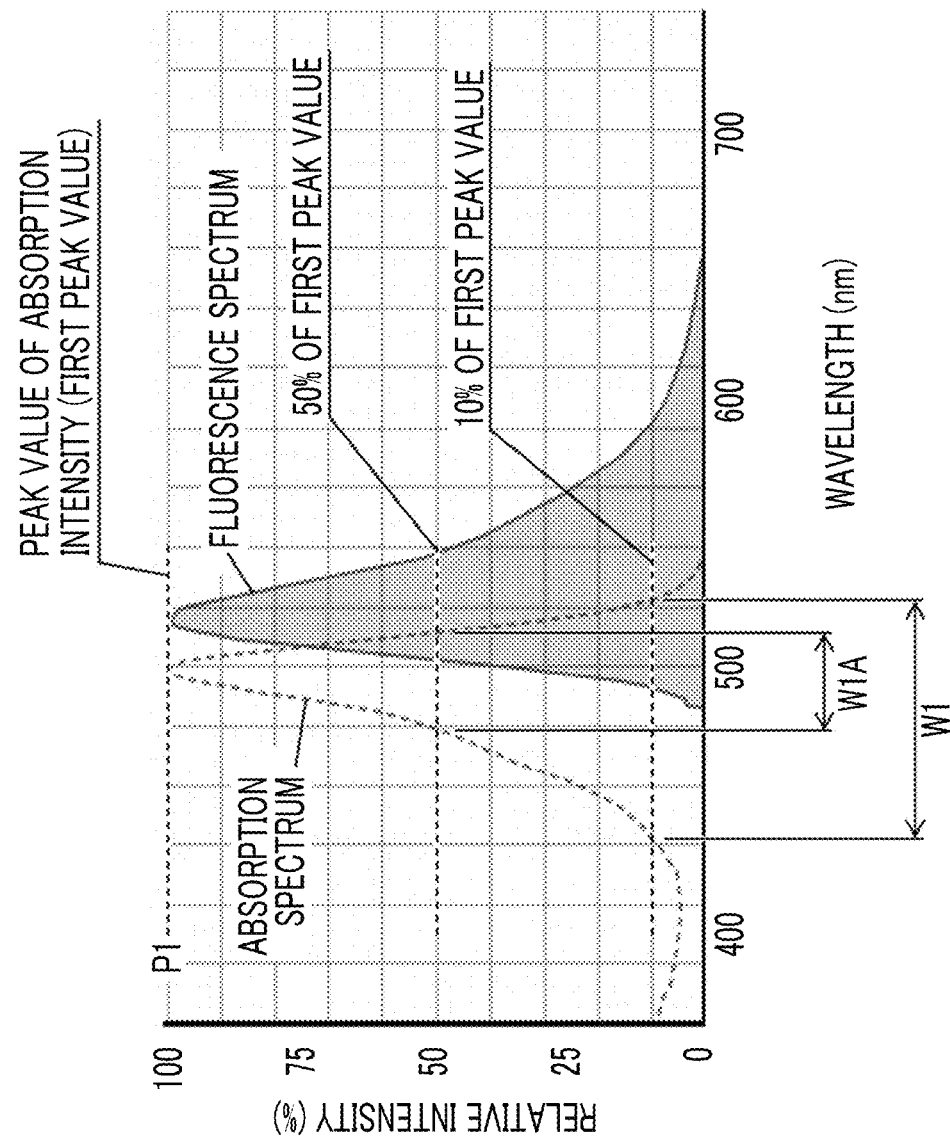
FIG. 7 is a graph showing the absorption spectrum and the fluorescence spectrum of fluorescein that is a fluorescent dye.

FIG. 7 is a graph showing the absorption spectrum and the fluorescence spectrum of fluorescein that is the fluorescent dye 33, and is a graph showing the condition for satisfying the criterion [B]. In FIG. 7, the absorption spectrum is shown by a dotted line and the fluorescence spectrum is shown by a solid line.

As shown in FIG. 7, the condition for satisfying the criterion [B] is a condition where at least a part of the wavelength region of the above-mentioned excitation light EL is included in a first wavelength region W1 in a case in which the peak value of the absorption intensity of the fluorescent dye 33 in the absorption spectrum of the fluorescent dye 33 is referred to as a first peak value P1 and a wavelength region where the absorption intensity of the fluorescent dye 33 is 10% or more of the first peak value P1 is referred to as the first wavelength region W1. Further, more preferably, the condition for satisfying the criterion [B] is a condition where at least a part of the wavelength region of the excitation light EL is included in a first wavelength region W1A in a case in which a wavelength region where the absorption intensity of the fluorescent dye 33 is 50% or more of the first peak value P1 is referred to as the first wavelength region W1A.

Condition for Satisfying Criterion [A]

Figure 8:
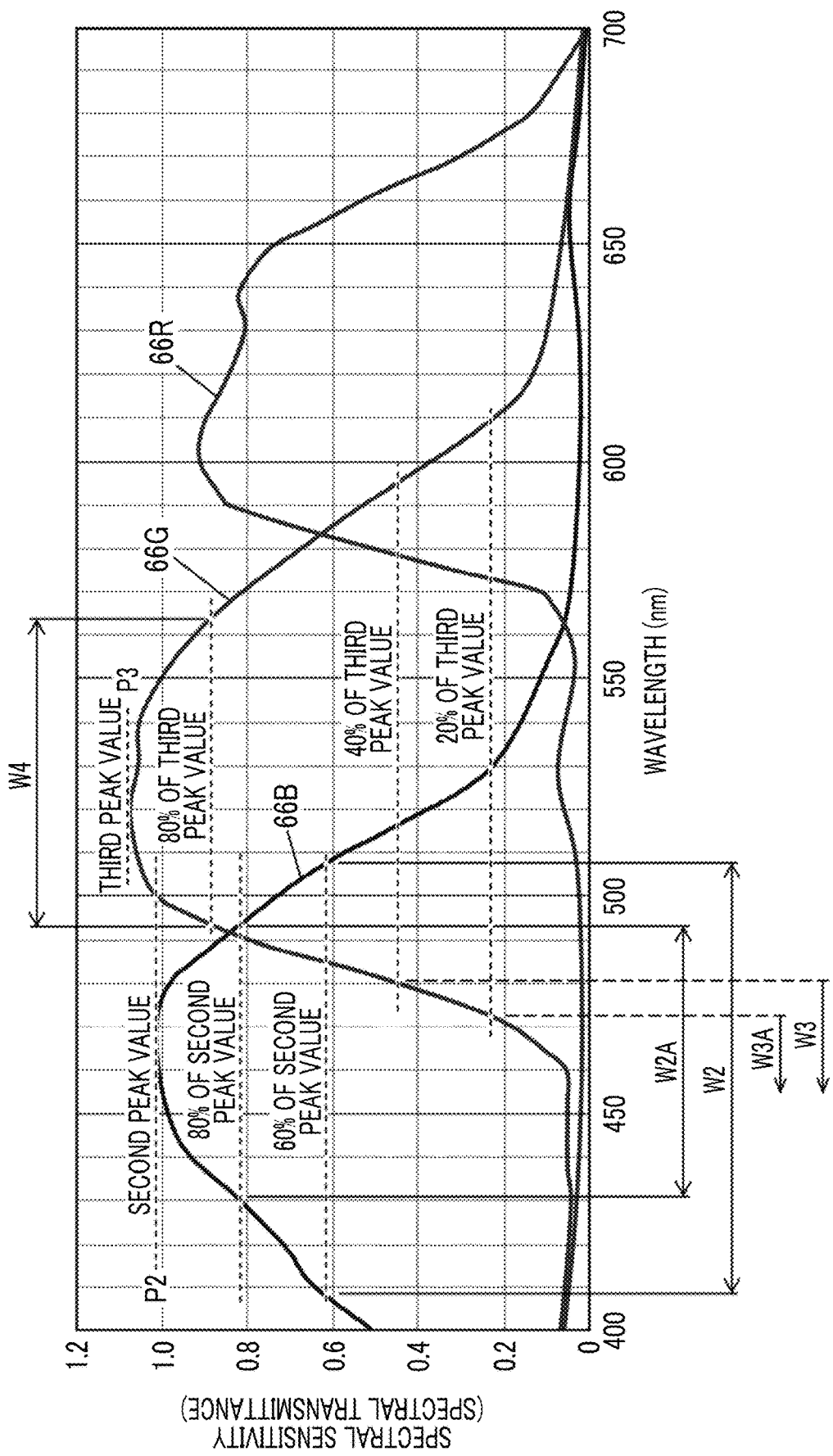
FIG. 8 is a graph showing the spectral sensitivity characteristics of the respective color pixels of the image pickup element.

Next, the condition for satisfying the criterion [A] will be described with reference to FIG. 8. Here, FIG. 8 is a graph showing the spectral sensitivity characteristics of the respective color pixels 53 of the image pickup element 49. FIG. 8 substantially shows the spectral transmittance characteristics of the respective color filters 54R, 54G, and 54B of the image pickup element 49, and shows the condition for satisfying the criterion [A]. In this specification, the spectral sensitivity characteristics of the respective color pixels 53 will be described as the meaning of the spectral transmittance characteristics of the respective color filters 54R, 54G, and 54B (the same shall apply hereinafter). The blue color filter 54B has a spectral transmittance characteristic 66B, the green color filter 54G has a spectral transmittance characteristic 66G, and the red color filter 54R has a spectral transmittance characteristic 66R. Here, the spectral transmittance characteristic 66B corresponds to a first spectral transmittance characteristic of the invention, the spectral transmittance characteristic 66G corresponds to a second spectral transmittance characteristic of the invention, and the wavelength regions of both the spectral transmittance characteristics 66B and 66G partially overlap each other.

As shown in FIG. 8, the peak value of the transmittance (spectral sensitivity) of the spectral transmittance characteristic 66B is referred to as a second peak value P2 and the peak value of the transmittance of the spectral transmittance characteristic 66G is referred to as a third peak value P3. Further, a wavelength region where the transmittance of the spectral transmittance characteristic 66B is 60% or more of the second peak value P2 is referred to as a second wavelength region W2, and a wavelength region where the transmittance of the spectral transmittance characteristic 66G is 40% or less of the third peak value P3 is referred to as a third wavelength region W3. Furthermore, a first condition for satisfying the criterion [A] is a condition where the wavelength region of the excitation light EL is included in the second wavelength region W2 and the third wavelength region W3.

It is more preferable that the above-mentioned second wavelength region W2 is a second wavelength region W2A which is a wavelength region where the transmittance of the spectral transmittance characteristic 66B is 80% or more of the second peak value P2. Further, it is more preferable that the above-mentioned third wavelength region W3 is a third wavelength region W3A which is a wavelength region where the transmittance of the spectral transmittance characteristic 66G is 20% or less of the third peak value P3.

A second condition for satisfying the criterion [A] is a condition where a wavelength (peak wavelength) at which the intensity of the fluorescence FL corresponds to a peak is included in a fourth wavelength region W4 in a case in which a wavelength region where the transmittance of the spectral transmittance characteristic 66G is 80% or more of the third peak value P3 is referred to as the fourth wavelength region W4.

As described above, in this embodiment, the fluorescent dye 33, a peak wavelength at which the spectrum of excitation light EL emitted from the light source device 11 and the intensity of excitation light EL are maximum, and the spectral transmittance characteristics of the color filters 54 of the image pickup element 49 are selected so that the above-mentioned criteria [A] and [B] are satisfied. Accordingly, a good fluorescence image 64 is obtained.

Action of Endoscope Apparatus of First Embodiment

Figure 9:
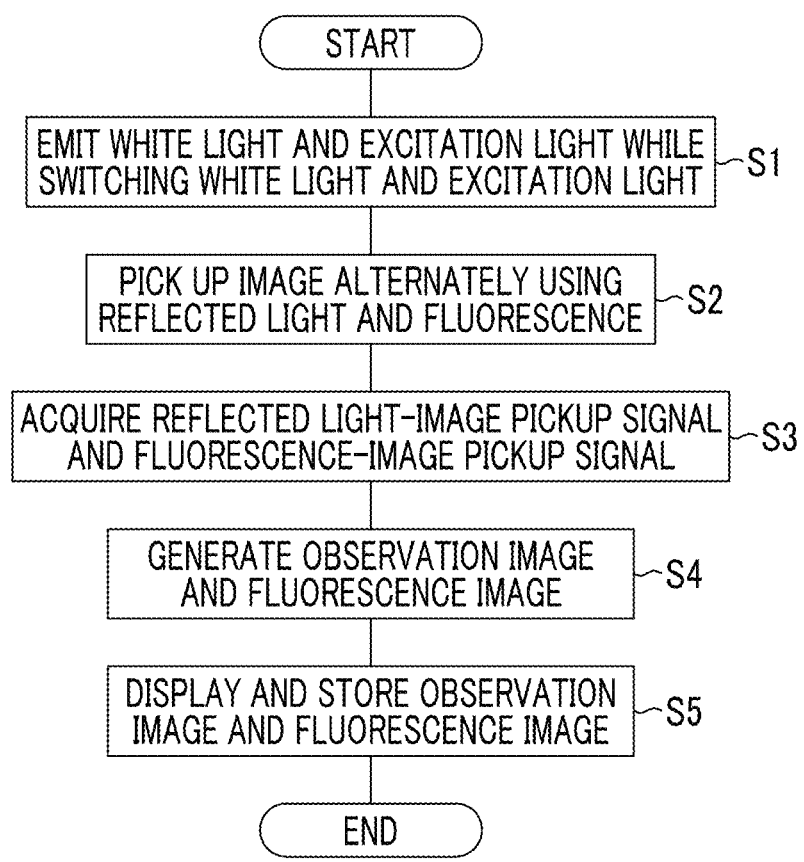
FIG. 9 is a flow chart showing the flow of processing of normal observation and fluorescence observation that are performed by the endoscope apparatus.

Next, the actions of the endoscope apparatus 9 having the above-mentioned configuration, particularly, normal observation and fluorescence observation will be described with reference to FIG. 9. Here, FIG. 9 is a flow chart showing the flow of processing of normal observation and fluorescence observation that are performed by the endoscope apparatus 9 (a method of operating the endoscope apparatus).

After each unit of the endoscope apparatus 9 is started up, the insertion part 15 is inserted into a subject by an operator. Then, in a case in which the operator turns on the multi-frame function of the endoscope apparatus 9 after the tip portion 21 of the insertion part 15 reaches a portion 34 to be observed, the light source control unit 40 of the light source device 11 controls the respective semiconductor light sources 36R, 36G, and 36B to make white light W and excitation light EL be alternately emitted as shown in already-described FIG. 5 or 6 (Step S1). Accordingly, white light W and excitation light EL are alternately applied to the portion 34 to be observed through the light guide 28 and the like of the endoscope 10.

The white light W, which is applied to the portion 34 to be observed, is reflected from the portion 34 to be observed and reflected light WR of the white light W is incident on the image pickup surface of the image pickup element 49 through the observation window 47 and the condenser lens 48. Further, excitation light EL, which is applied to the portion 34 to be observed, allows the fluorescent dye 33, which is contained in the portion 34 to be observed, to be excited to emit light and fluorescence FL emitted from the fluorescent dye 33 is incident on the image pickup surface of the image pickup element 49 through the observation window 47 and the condenser lens 48. In this case, in this embodiment, the fluorescent dye 33 and the wavelength region of excitation light EL emitted from the light source device 11 are appropriately selected so that the criterion [B] is satisfied (see FIG. 7). Accordingly, already-described "fluorescence emission intensity" is sufficiently increased.

Then, reflected light WR and fluorescence FL are alternately incident on the image pickup surface of the image pickup element 49 in accordance with the alternate emission of white light W and excitation light EL from the light source device 11.

The drive control unit 55 of the processor 12 controls the drive of the image pickup element 49 through the drive circuit 50 to make the image pickup element 49 sequentially pick up images using reflected light WR and fluorescence FL that are alternately incident on the image pickup surface of the image pickup element 49 (Step S2). Accordingly, reflected light-image pickup signals IS and fluorescence-image pickup signals IF are alternately output from the image pickup element 49. In this case, as described in already-described FIGS. 5 and 6, the drive control unit 55 compensates a difference in intensity between the reflected light-image pickup signal IS and the fluorescence-image pickup signal IF by making a time in which electrical charges are accumulated in the respective pixels 53 of the image pickup element 49 during the fluorescence observation be longer than a time in which electrical charges are accumulated in the respective pixels 53 during the normal observation.

Further, in this embodiment, the fluorescent dye 33, the excitation light EL emitted from the light source device 11, and the spectral transmittance characteristics of the color filters 54 of the image pickup element 49 are appropriately selected so that the above-mentioned criterion [A] is satisfied. Accordingly, already-described "sensor color separation" is also good.

The reflected light-image pickup signals IS and the fluorescence-image pickup signals IF, which are alternately output from the image pickup element 49, are input to the image signal acquisition unit 56 of the processor 12 through the image signal output unit 52, the signal cable 29, the connector 30B, and the like after being subjected to various types of signal processing by the signal processing unit 51. Accordingly, the image signal acquisition unit sequentially acquires the reflected light-image pickup signals IS and the fluorescence-image pickup signals IF that are sequentially output from the endoscope 10 (Step S3). Then, the image signal acquisition unit 56 outputs a newly acquired reflected light-image pickup signal IS to the observation image generating unit 60 and outputs a newly acquired reflected light-image pickup signal IS and a newly acquired fluorescence-image pickup signal IF to the fluorescence image generating unit 61.

Whenever sequentially acquiring new reflected light-image pickup signals IS from the image signal acquisition unit 56, the observation image generating unit 60 generates observation images 63 on the basis of the new reflected light-image pickup signal IS and sequentially outputs the generated observation images 63 to the display control unit 58 and the storage unit 59 (Step S4).

On the other hand, whenever acquiring a new reflected light-image pickup signal IS and a new fluorescence-image pickup signal IF from the image signal acquisition unit 56, the fluorescence image generating unit 61 generates a simple fluorescence image 64a on the basis of the new fluorescence-image pickup signal IF, generates a background image 64b on the basis of the reflected light-image pickup signal IS, and combines the simple fluorescence image 64a with the background image 64b to generate a fluorescence image 64 (Step S4). Then, the fluorescence image generating unit 61 sequentially outputs the generated fluorescence image 64 to the display control unit 58 and the storage unit 59.

The display control unit 58 makes the monitor 13 display the observation image 63 and the fluorescence image 64, which are sequentially input from the observation image generating unit 60 and the fluorescence image generating unit 61, in the form of a moving image and the storage unit 59 stores the observation image 63 and the fluorescence image 64 that are sequentially input from the observation image generating unit 60 and the fluorescence image generating unit 61 (Step S5).

Effect of Endoscope Apparatus of First Embodiment

As described above, according to the endoscope apparatus 9 of the first embodiment, the fluorescent dye 33, the light source device 11 (excitation light EL), and the spectral transmittance characteristics of the color filters 54 of the image pickup element 49 are appropriately selected so that the above-mentioned criteria [A] and [B] are satisfied. Accordingly, a good fluorescence image 64 is obtained without the disposition of a filter for fluorescence observation, a filter for reducing the intensity of excitation light, and the like in the tip portion 21. As a result, both the normal observation and the fluorescence observation can be performed by a simple configuration.

Second Embodiment

Fluorescent Dye: Rhodamine Green

Fluorescein has been used as the fluorescent dye 33 in the first embodiment, but a fluorescent dye 33 other than fluorescein may be used. For example, Rhodamine Green may be used as the fluorescent dye 33.

Figure 10:
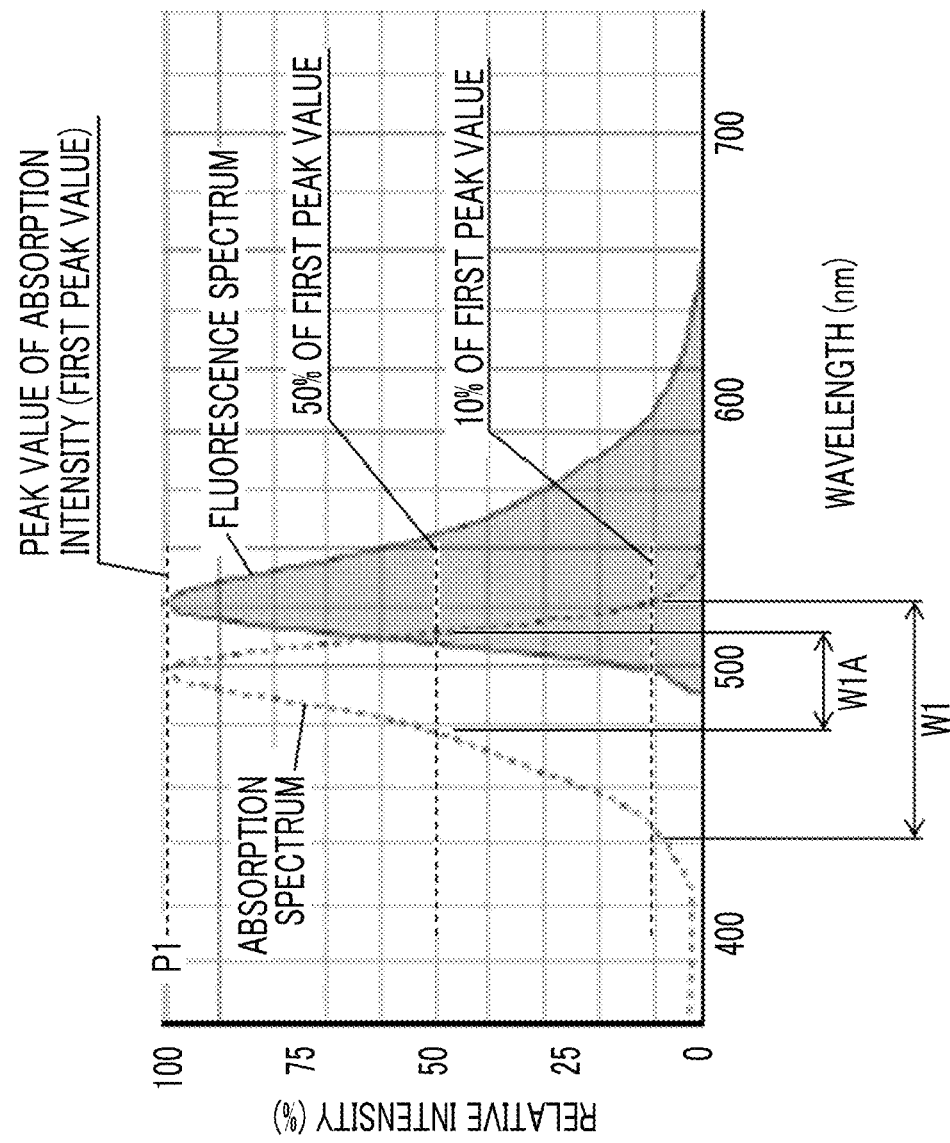
FIG. 10 is a graph showing the absorption spectrum and the fluorescence spectrum of Rhodamine Green.

FIG. 10 is a graph showing the absorption spectrum and the fluorescence spectrum of Rhodamine Green. As shown in FIG. 10, Rhodamine Green has substantially the same absorption spectrum and fluorescence spectrum as those of fluorescein shown in already-described FIG. 7. Accordingly, Rhodamine Green can be used instead of fluorescein without the change of the basic configuration of the apparatus.

As in the first embodiment, the condition of the wavelength region of excitation light EL, which satisfies the already-described criterion [B], is a condition where at least a part of the wavelength region of excitation light EL is included in the already-described first wavelength region W1, more preferably, is included in the already-described first wavelength region W1A. Further, since a condition for satisfying the already-described criterion [B] is the same as that of the first embodiment shown in FIG. 8, the specific description thereof will be omitted.

Fluorescent Dye: PpIX

Further, protoporphyrin IX (PpIX) of which Stokes shift is larger than the Stokes shift of fluorescein may be used as the fluorescent dye 33. PpIX is a material converted from 5-aminolevulinic acid (5-ALA), which is used for photodynamic diagnosis (PDD), in a cell by a metabolic enzyme.

Figure 11:
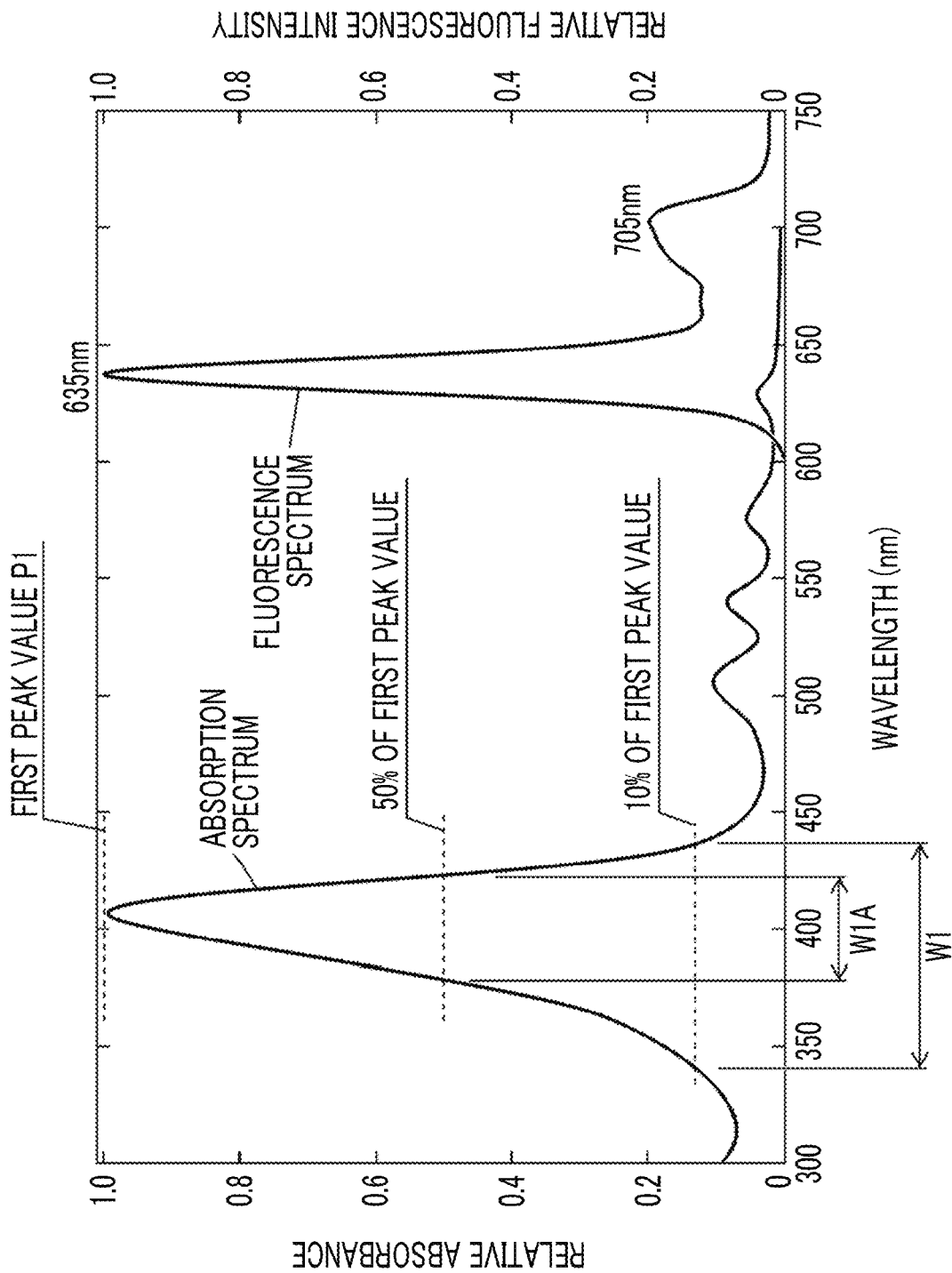
FIG. 11 is a graph showing the absorption spectrum and the fluorescence spectrum of PpIX.

FIG. 11 is a graph showing the absorption spectrum and the fluorescence spectrum of PpIX. As shown in FIG. 11, PpIX can be excited by blue light BL or purple light VL (see FIG. 3) and emits red fluorescence FL. For this purpose, the light source device 11 may be separately provided with a semiconductor light source for emitting purple light VL (see FIG. 17). In a case in which PpIX is used as the fluorescent dye 33 as described above, blue light BL, purple light VL, or resultant light of both the blue light BL and the purple light VL is used as the excitation light EL.

As in the first embodiment, the condition of the wavelength region of excitation light EL, which satisfies the already-described criterion [B], is a condition where at least a part of the wavelength region of the excitation light EL is included in the already-described first wavelength region W1, more preferably, is included in the already-described first wavelength region W1A.

Since fluorescence FL emitted from PpIX is red fluorescence, the fluorescence FL is detected by a red pixel 53. Accordingly, in this case, a red color filter 54R corresponds to the second color filter of the invention and the spectral transmittance characteristic 66R of the red color filter 54R corresponds to a second spectral transmittance characteristic of the invention. Further, the wavelength regions of the respective spectral transmittance characteristics 66B and 66R are separated from each other.

Figure 12:
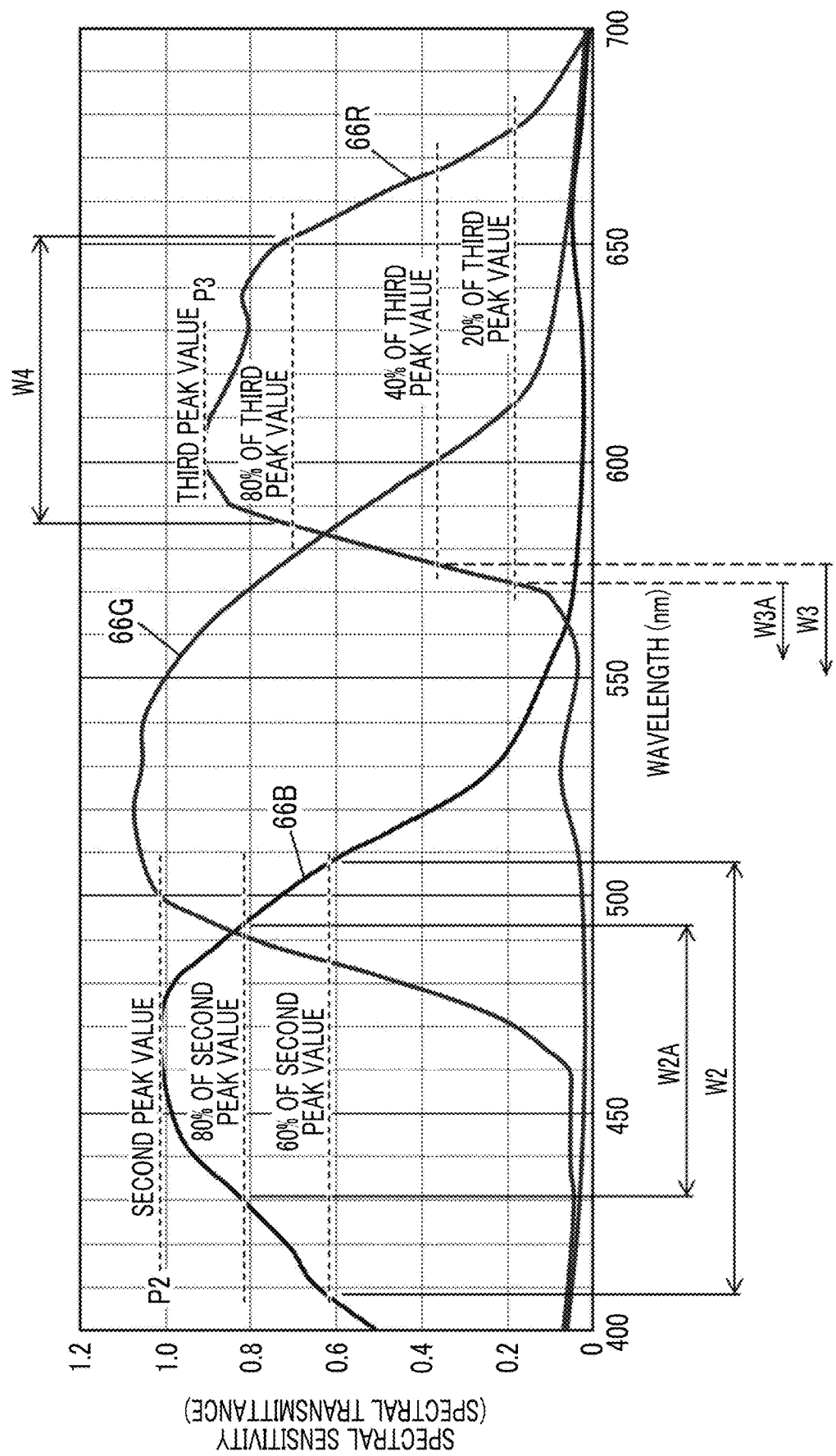
FIG. 12 is a graph showing the spectral sensitivity characteristics of the respective color pixels of the image pickup element.

FIG. 12 is a graph showing the spectral sensitivity characteristics of the respective color pixels 53 of the image pickup element 49. As in already-described FIG. 8, FIG. 12 substantially shows the spectral transmittance characteristics of the respective color filters 54R, 54G, and 54B of the image pickup element 49, and shows a condition for satisfying the criterion [A] in a case in which PpIX is used as the fluorescent dye 33. As shown in FIG. 12, the peak value of the transmittance of the spectral transmittance characteristic 66R is referred to as a third peak value P3 in a case in which PpIX is used as the fluorescent dye 33. Further, a wavelength region where the transmittance of the spectral transmittance characteristic 66R is 40% or less of the third peak value P3 is referred to as a third wavelength region W3, and a wavelength region where the transmittance of the spectral transmittance characteristic 66R is 20% or less of the third peak value P3 is referred to as a third wavelength region W3A. Furthermore, a wavelength region where the transmittance of the spectral transmittance characteristic 66R is 80% or more of the third peak value P3 is referred to as a fourth wavelength region W4.

Accordingly, as in the first embodiment, a first condition for satisfying the criterion [A] is a condition where the wavelength region of the excitation light EL is included in the second wavelength region W2 and the third wavelength region W3 and a second condition for satisfying the criterion [A] is a condition where a wavelength (peak wavelength) at which the intensity of the fluorescence FL corresponds to a peak is included in the fourth wavelength region W4. It is more preferable that the second wavelength region W2 is a second wavelength region W2A and the third wavelength region W3 is a third wavelength region W3A.

Even though PpIX is used as the fluorescent dye 33 as described above, a good fluorescence image 64 is obtained in a case in which a peak wavelength at which the spectrum of excitation light EL emitted from the light source device 11 and the intensity of excitation light EL are maximum and the spectral transmittance characteristics of the color filters 54 of the image pickup element 49 are selected so that the above-mentioned criteria [A] and [B] are satisfied. Particularly, since the wavelength region of excitation light EL (blue light BL) and the wavelength region of red fluorescence FL are separated from each other, color separation is good in a case in which excitation light EL and fluorescence FL are detected by the image pickup element 49. Accordingly, a good fluorescence image 64 is obtained.

Fluorescent Dye: SYPRO Red

Further, "SYPRO Red" may be used as the fluorescent dye 33 instead of the above-mentioned fluorescein and the like.

Figure 13:
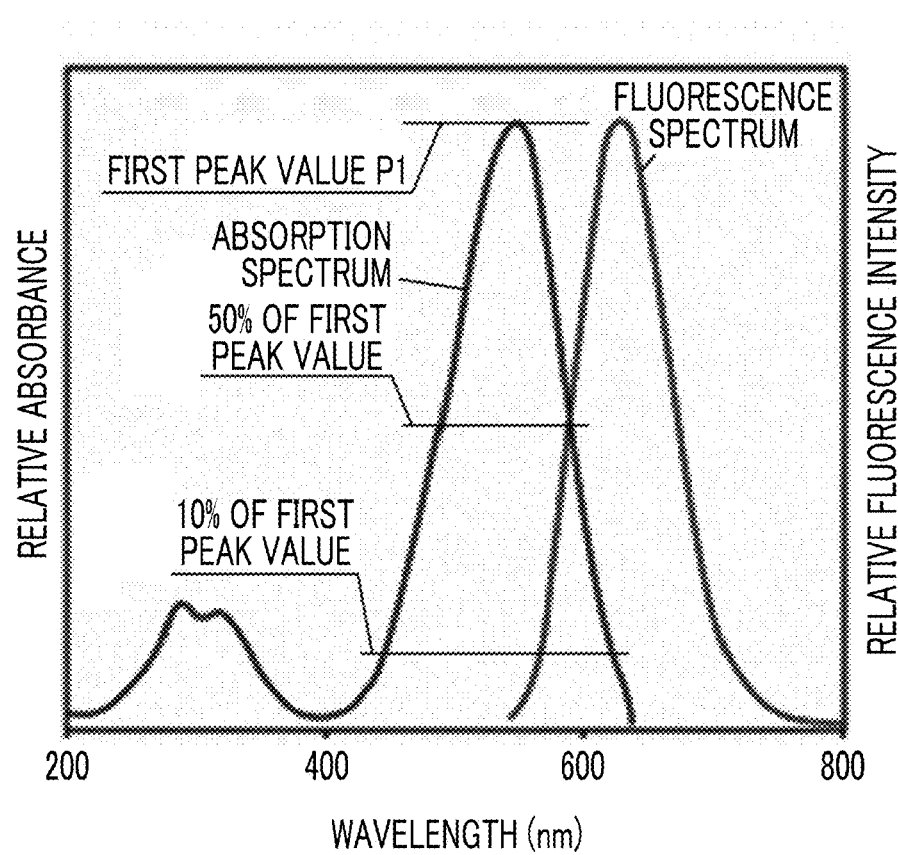
FIG. 13 is a graph showing the absorption spectrum and the fluorescence spectrum of SYPRO Red.

FIG. 13 is a graph showing the absorption spectrum and the fluorescence spectrum of SYPRO Red. As shown in FIG. 13, SYPRO Red has an absorption peak wavelength of about 550 nm, and absorbs green light GL as excitation light EL and emits fluorescence FL (red fluorescence) having a wavelength of about 630 nm. Accordingly, in a case in which SYPRO Red is used as the fluorescent dye 33, a green color filter 54G corresponds to the first color filter of the invention and the spectral transmittance characteristic 66G of the green color filter 54G corresponds to the first spectral transmittance characteristic of the invention. Furthermore, a red color filter 54R corresponds to the second color filter of the invention and the spectral transmittance characteristic 66R of the red color filter 54R corresponds to the second spectral transmittance characteristic of the invention.

As in the first embodiment, the condition of the wavelength region of excitation light EL (green light GL), which satisfies the already-described criterion [B], is a condition where at least a part of the wavelength region of the excitation light EL is included in the already-described first wavelength region W1, more preferably, is included in the already-described first wavelength region W1A.

Figure 14:
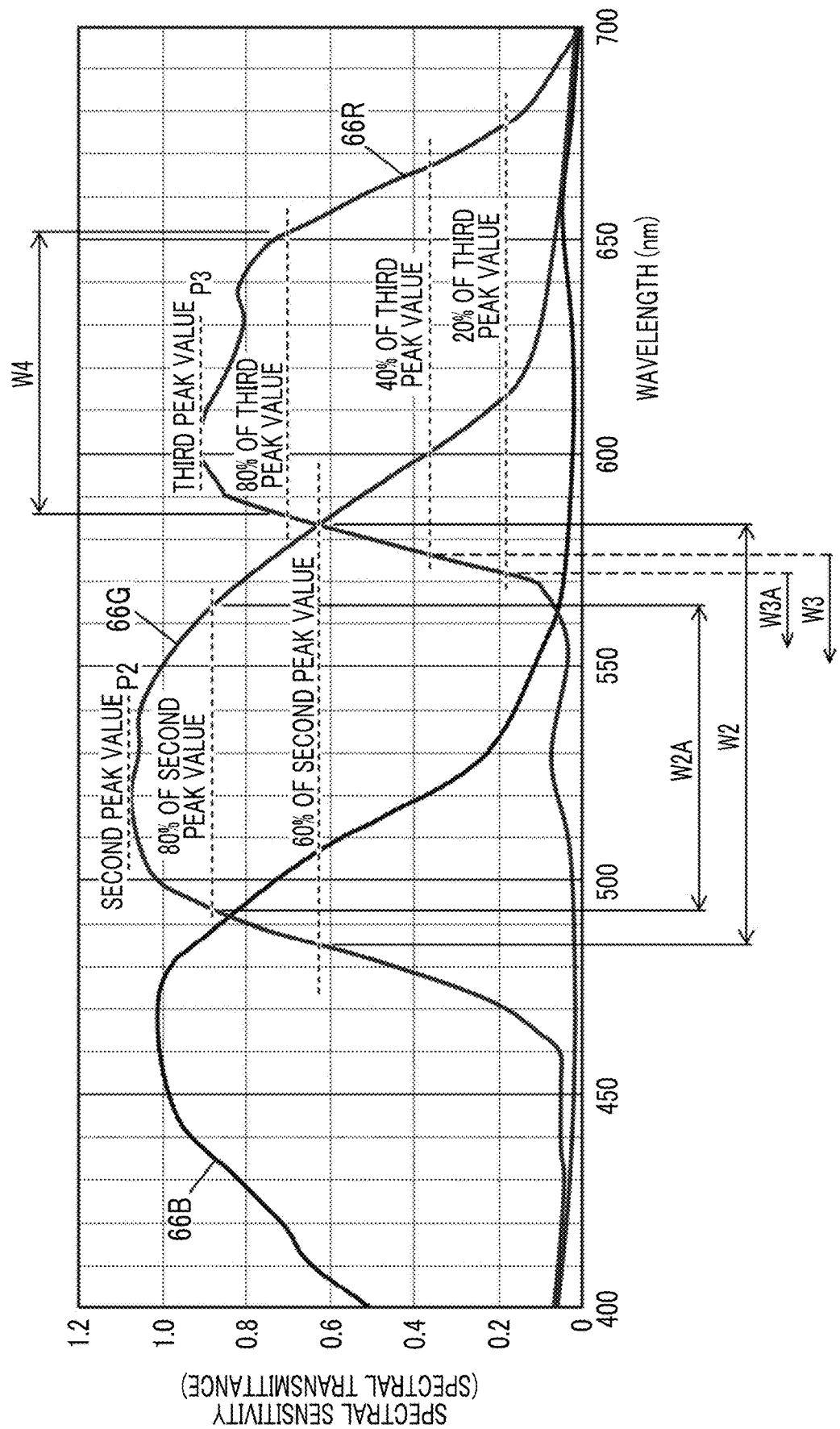
FIG. 14 is a graph showing the spectral sensitivity characteristics of the respective color pixels of the image pickup element.

FIG. 14 is a graph showing the spectral sensitivity characteristics of the respective color pixels 53 of the image pickup element 49. As in already-described FIG. 8, FIG. 14 substantially shows the spectral transmittance characteristics of the respective color filters 54R, 54G, and 54B of the image pickup element 49, and shows a condition for satisfying the criterion [A] in a case in which SYPRO Red is used as the fluorescent dye 33.

As shown in FIG. 14, the peak value of the transmittance of the spectral transmittance characteristic 66G is referred to as a second peak value P2 and the peak value of the transmittance of the spectral transmittance characteristic 66R is referred to as a third peak value P3 in a case in which SYPRO Red is used as the fluorescent dye 33. Further, a wavelength region where the transmittance of the spectral transmittance characteristic 66B is 60% or more of the second peak value P2 is referred to as a second wavelength region W2, and a wavelength region where the transmittance of the spectral transmittance characteristic 66B is 80% or more of the second peak value P2 is referred to as a second wavelength region W2A. Furthermore, a wavelength region where the transmittance of the spectral transmittance characteristic 66R is 40% or less of the third peak value P3 is referred to as a third wavelength region W3 and a wavelength region where the transmittance of the spectral transmittance characteristic 66R is 20% or less of the third peak value P3 is referred to as a third wavelength region W3A. Moreover, a wavelength region where the transmittance of the spectral transmittance characteristic 66R is 80% or more of the third peak value P3 is referred to as a fourth wavelength region W4.

Accordingly, as in the first embodiment, a first condition for satisfying the criterion [A] is a condition where the wavelength region of green light GL used as the excitation light EL is included in at least the second wavelength region W2 and the third wavelength region W3 and a second condition for satisfying the criterion [A] is a condition where a wavelength (peak wavelength) at which the intensity of the fluorescence FL corresponds to a peak is included in the fourth wavelength region W4. It is more preferable that the second wavelength region W2 is the second wavelength region W2A and the third wavelength region W3 is the third wavelength region W3A.

Even though SYPRO Red is used as the fluorescent dye 33 as described above, a good fluorescence image 64 is obtained in a case in which a peak wavelength at which the spectrum of excitation light EL emitted from the light source device 11 and the intensity of excitation light EL are maximum and the spectral transmittance characteristics of the color filters 54 of the image pickup element 49 are selected so that the above-mentioned criteria [A] and [B] are satisfied.

Modification Example of Light Source Device in Case in which SYPRO Red is Used

In a case in which SYPRO Red is used as the fluorescent dye 33, green light GL is used as excitation light EL. However, since light of a wavelength region in which a wavelength is equal to or larger than a predetermined wavelength, of green light GL is transmitted through a red color filter 54R as shown in already-described FIG. 8, the excitation light EL (green light GL) is detected by a red pixel 53 as in the case of fluorescence FL. As a result, since there is a concern that it may be difficult to separate the excitation light EL from the fluorescence FL, that is, already-described "sensor color separation" may deteriorate, there is a concern that an S/N ratio (signal-to-noise ratio) in the case of detection of the fluorescence FL may deteriorate.

Figure 15:
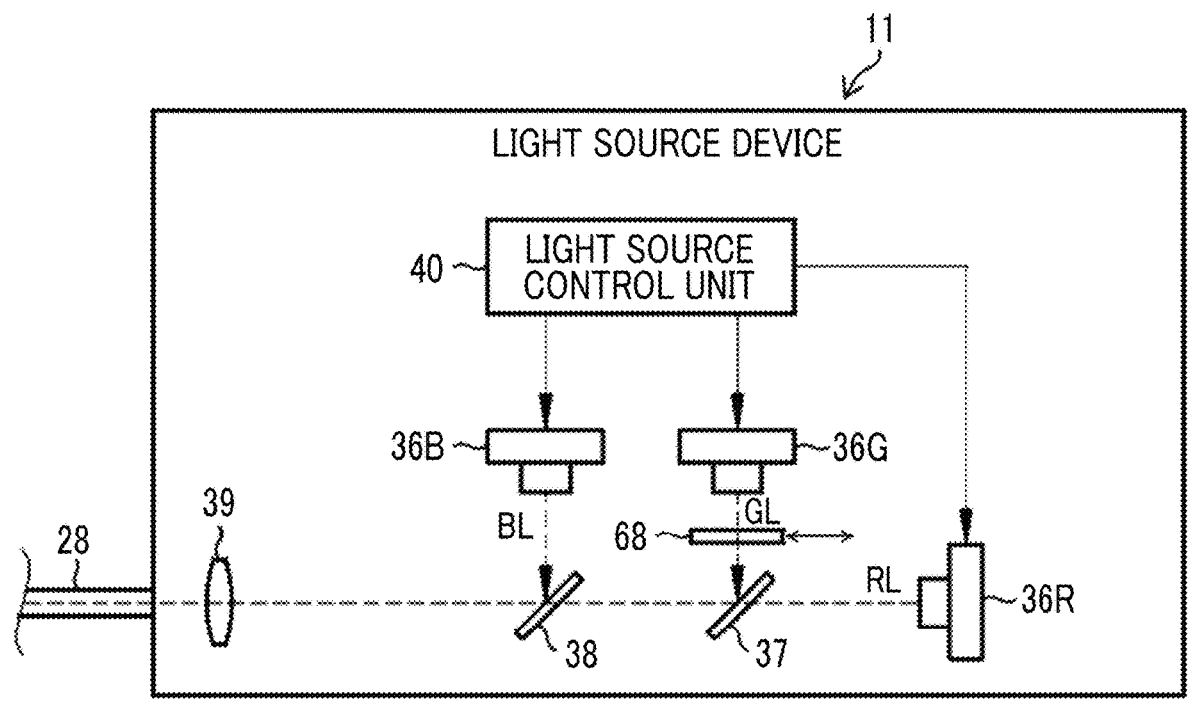
FIG. 15 is a block diagram showing a modification example of the light source device in a case in which SYPRO Red is used as a fluorescent dye.

FIG. 15 is a block diagram showing a modification example of the light source device 11 in a case in which SYPRO Red is used as the fluorescent dye 33. As shown in FIG. 15, a wavelength limiting filter 68, such as a band pass filter, for limiting the wavelength region of the green light GL is removably disposed on the optical path of green light GL (excitation light EL) emitted from the semiconductor light source 36G of the light source device 11. The wavelength limiting filter 68 is disposed on the optical path of green light GL (excitation light EL) during the fluorescence observation and is retracted from the optical path of green light GL during the normal observation, by a filter moving mechanism (not shown).

Figure 16:
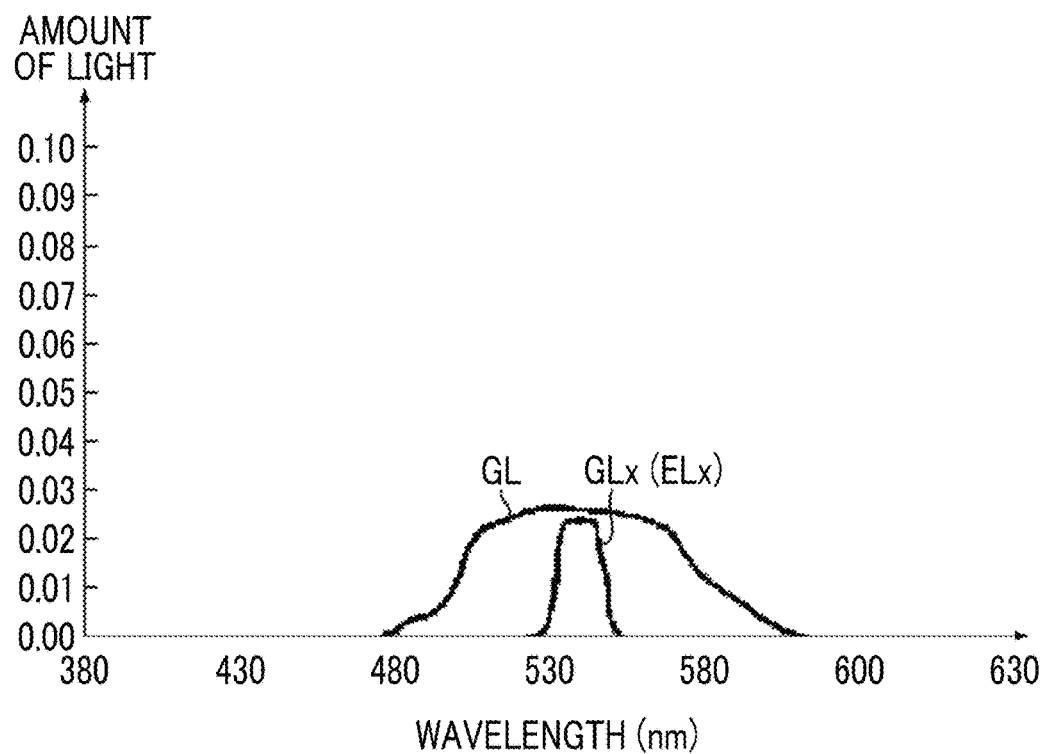
FIG. 16 is a diagram illustrating the transmittance-wavelength characteristics of a wavelength limiting filter.

FIG. 16 is a diagram illustrating the transmittance-wavelength characteristics of the wavelength limiting filter 68. As shown in FIG. 16, the wavelength limiting filter 68 limits the wavelength region of green light GL (excitation light EL) emitted from the semiconductor light source 36G and transmits only narrow-band green light GLx (narrow-band excitation light ELx) that is narrow-band light having, for example, a center wavelength of about 550 nm. The wavelength region of the narrow-band green light GLx (narrow-band excitation light ELx) is not particularly limited as long as being a wavelength region (see FIG. 8) where the transmittance of the light at the red color filter 54R is low.

Since a portion 34 to be observed is irradiated with the narrow-band excitation light ELx through the wavelength limiting filter 68 during the fluorescence observation as described above, the detection of the narrow-band excitation light ELx at the red pixel 53 is substantially prevented. As a result, since the narrow-band excitation light ELx and the fluorescence FL are separated from each other, already-described "sensor color separation" is good and an S/N ratio in the case of detection of the fluorescence FL is also good. Further, since the wavelength limiting filter 68 may be disposed not in the tip portion 21 of the endoscope 10 having no extra arrangement space therein but in the light source device 11 relatively having an extra arrangement space therein, a simple configuration can be realized.

Instead of the wavelength limiting filter 68 that is removably disposed on the optical path of green light GL emitted from the semiconductor light source 36G, a narrow-band light source, which emits narrow-band green light GLx (narrow-band excitation light ELx) of which the wavelength is limited in advance, may be disposed as the semiconductor light source 36G.

Third Embodiment

Next, an endoscope apparatus 9A of a third embodiment of the invention will be described. In the first embodiment, normal observation in which reflected light WR of white light W reflected from a portion 34 to be observed, that is, the white light image of the portion 34 to be observed is observed is performed as the illumination light observation of the invention. In contrast, in the third embodiment, narrow-band light observation in which a surface-layer blood vessel image and a middle-layer blood vessel image of a portion 34 to be observed are observed using narrow-band light of which the wavelength is limited is performed in addition to the normal observation as the illumination light observation of the invention. The narrow-band light observation is performed at the same time as the already-described fluorescence observation. In the third embodiment, already-described SYPRO Red, which absorbs green light GL as excitation light EL and emits red fluorescence FL (red fluorescence), and the like are used as the fluorescent dye 33.

Figure 17:
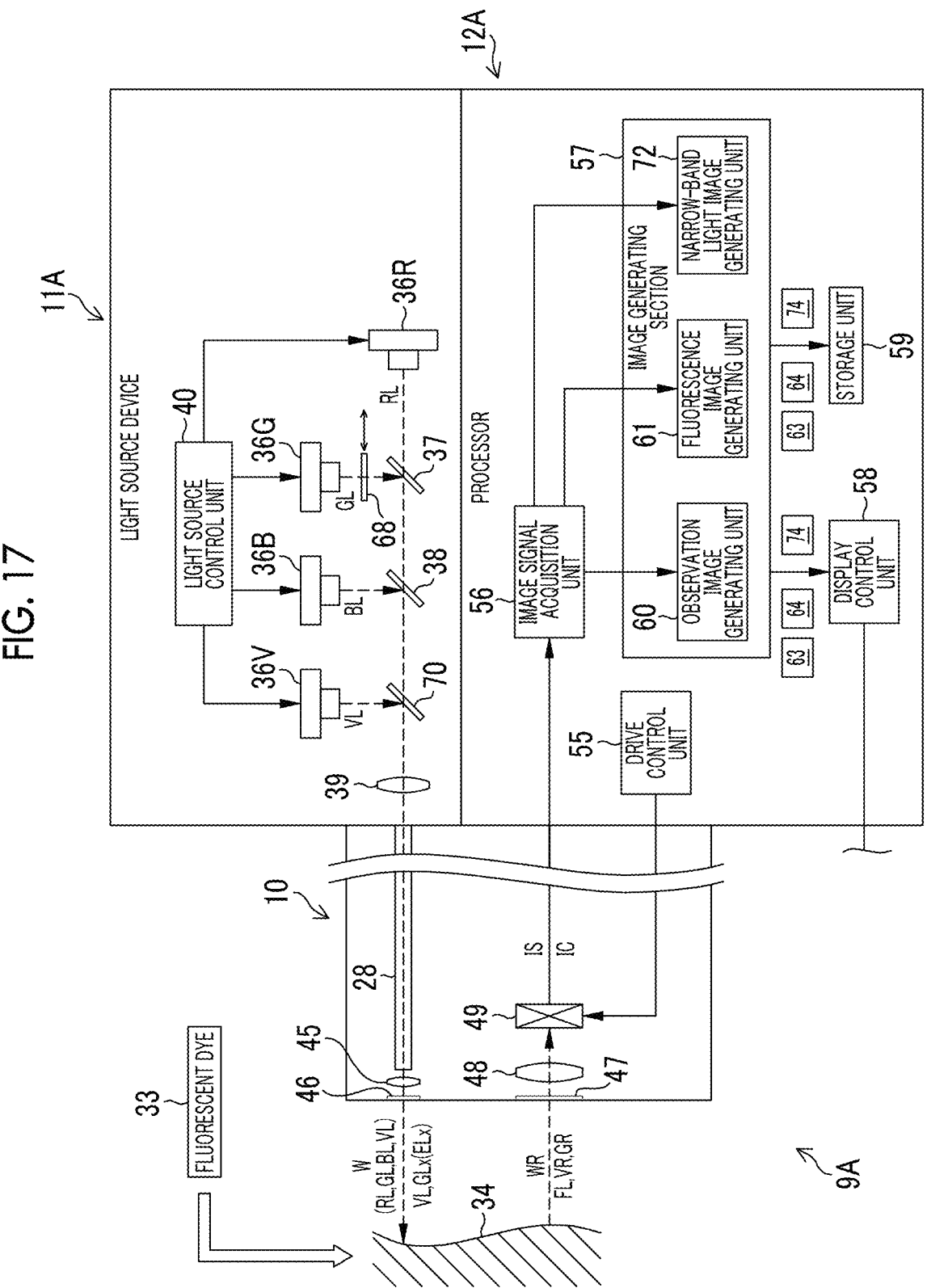
FIG. 17 is a block diagram showing the configuration of an endoscope apparatus of a third embodiment.

FIG. 17 is a block diagram showing the configuration of the endoscope apparatus 9A of the third embodiment. As shown in FIG. 17, the configuration of the endoscope apparatus 9A is basically the same as the configuration of the endoscope apparatus 9 of each of the above-mentioned embodiments except that the endoscope apparatus 9A includes a light source device 11A and a processor 12A different from the light source device and the processor of each of the above-mentioned embodiments. For this reason, components having the same functions and configurations as those of each of the above-mentioned embodiments will be denoted by the same reference numerals as the reference numerals of each of the above-mentioned embodiments, and the description thereof will be omitted.

The configuration of the light source device 11A is basically the same as the configuration of the light source device 11 shown in already-described FIG. 15 except that a semiconductor light source 36V for emitting purple light VL is provided in parallel with the already-described semiconductor light sources 36G and 36B and a dichroic filter 70 is disposed at an intersection between the optical path of purple light VL and the optical path of red light RL.

During the normal observation, the dichroic filter 70 transmits red light RL, green light GL, and blue light BL, which are incident from the dichroic filter 38, and reflects purple light VL, which is incident from the semiconductor light source 36V, to the lens 39. Further, during the fluorescence observation and the narrow-band light observation, the dichroic filter 70 transmits narrow-band green light GLx incident from the dichroic filter 38 and reflects the purple light VL, which is incident from the semiconductor light source 36V, to the lens 39.

Figure 18:
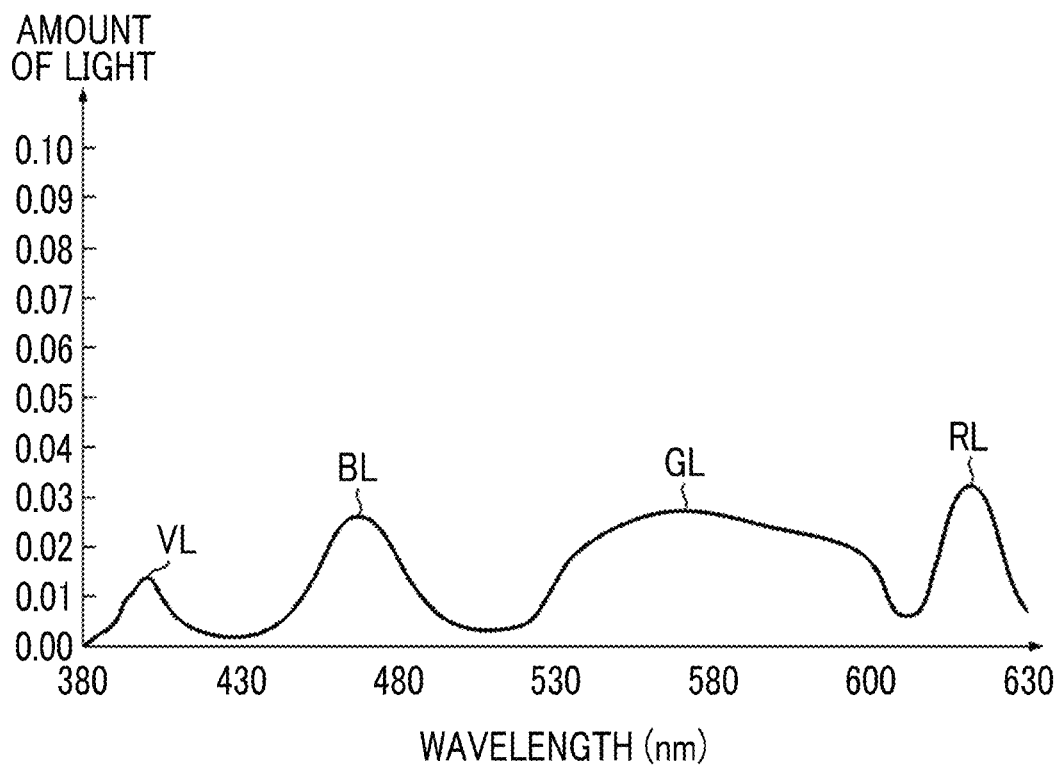
FIG. 18 is a graph showing an example of the spectral characteristics of respective color lights emitted from a light source device in a case in which normal observation is performed.
Figure 19:
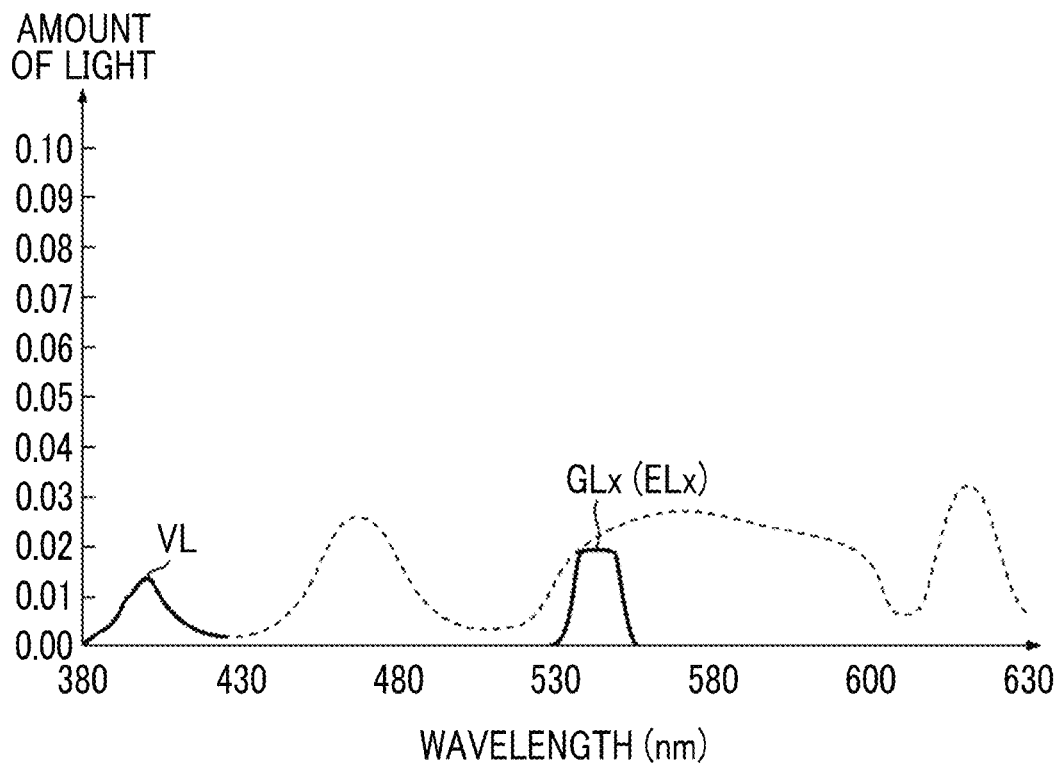
FIG. 19 is a graph showing an example of the spectral characteristics of respective color lights emitted from the light source device in a case in which fluorescence observation and narrow-band light observation are performed.

FIG. 18 is a graph showing an example of the spectral characteristics of the respective color lights emitted from the light source device 11A in a case in which the normal observation is performed, and FIG. 19 is a graph showing an example of the spectral characteristics of the respective color lights emitted from the light source device 11A in a case in which the fluorescence observation and the narrow-band light observation are performed.

As shown in FIG. 18, the light source control unit 40 of the third embodiment simultaneously operates the respective semiconductor light sources 36R, 36G, 36B, and 36V in a case in which the normal observation is performed. In this case, the already-described wavelength limiting filter 68 is retracted from the optical path of the green light GL. Accordingly, white light W including red light RL, green light GL, blue light BL, and purple light VL is emitted from the light source device 11A, and is applied to the portion 34 to be observed through the light guide 28 and the like of the endoscope 10. Then, an image is picked up using reflected light WR of the white light W, which is reflected from the portion 34 to be observed, by the image pickup element 49 of the endoscope 10 and a reflected light-image pickup signal IS is output to the processor 12A.

As shown in FIG. 19, the light source control unit 40 of the third embodiment simultaneously operates two types of semiconductor light sources 36G and 36V in a case in which the fluorescence observation and the narrow-band light observation are performed. Further, in this case, the already-described wavelength limiting filter 68 is inserted onto the optical path of the green light GL. Accordingly, purple light VL and narrow-band green light GLx (narrow-band excitation light ELx) are emitted from the light source device 11A and are applied to the portion 34 to be observed through the light guide 28 and the like of the endoscope 10.

In this case, the fluorescent dye 33 contained in the portion 34 to be observed is excited by the narrow-band excitation light ELx so as to emit light and red fluorescence FL is generated. Further, narrow-band purple light VL is reflected from the portion 34 to be observed, so that reflected light VR, which is the image light of a surface-layer blood vessel image of the portion 34 to be observed, is generated. Furthermore, the narrow-band green light GLx (narrow-band excitation light ELx) is reflected from the portion 34 to be observed, so that reflected light GR, which is the image light of a middle-layer blood vessel image of the portion 34 to be observed, is generated. Since the narrow-band light observation in which the surface-layer blood vessel image and the middle-layer blood vessel image are obtained is a publicly known technique, the principle thereof will be omitted here. Then, an image is picked up using resultant light of the fluorescence FL and the reflected lights VR and GR by the image pickup element 49 of the endoscope 10, and a resultant light-image pickup signal IC is output to the processor 12A.

Since the normal observation, the fluorescence observation, and the narrow-band light observation are performed simultaneously (in parallel), the emission of white light W and the emission of purple light VL and narrow-band green light GLx (narrow-band excitation light ELx) are alternately switched in the light source control unit 40 of the third embodiment as in the first embodiment. Accordingly, the image pickup element 49 alternately outputs the reflected light-image pickup signals IS and the resultant light-image pickup signals IC to the processor 12A.

Returning to FIG. 17, the configuration of the processor 12A is basically the same as the configuration of the processor 12 of each of the above-mentioned embodiments except that the image generating section 57 functions as a narrow-band light image generating unit 72 in addition to the observation image generating unit 60 and the fluorescence image generating unit 61 having been already described.

As in each of the above-mentioned embodiments, whenever acquiring a new reflected light-image pickup signal IS from the image signal acquisition unit 56, the observation image generating unit 60 of the third embodiment generates an observation image 63 on the basis of the new reflected light-image pickup signal IS and sequentially outputs the generated observation image 63 to the display control unit 58 and the storage unit 59.

Whenever acquiring a new reflected light-image pickup signal IS and a new resultant light-image pickup signal IC from the image signal acquisition unit 56, the fluorescence image generating unit 61 of the third embodiment generates a fluorescence image 64 on the basis of the new reflected light-image pickup signal IS and the new resultant light-image pickup signal IC. Further, whenever acquiring a new resultant light-image pickup signal IC from the image signal acquisition unit 56, the narrow-band light image generating unit 72 generates the surface-layer blood vessel image and the middle-layer blood vessel image of the portion 34 to be observed, that is, a narrow-band light image 74 of the portion 34 to be observed, which is an image in which blood vessels are emphasized, on the basis of the new resultant light-image pickup signal IC.

Figure 20:
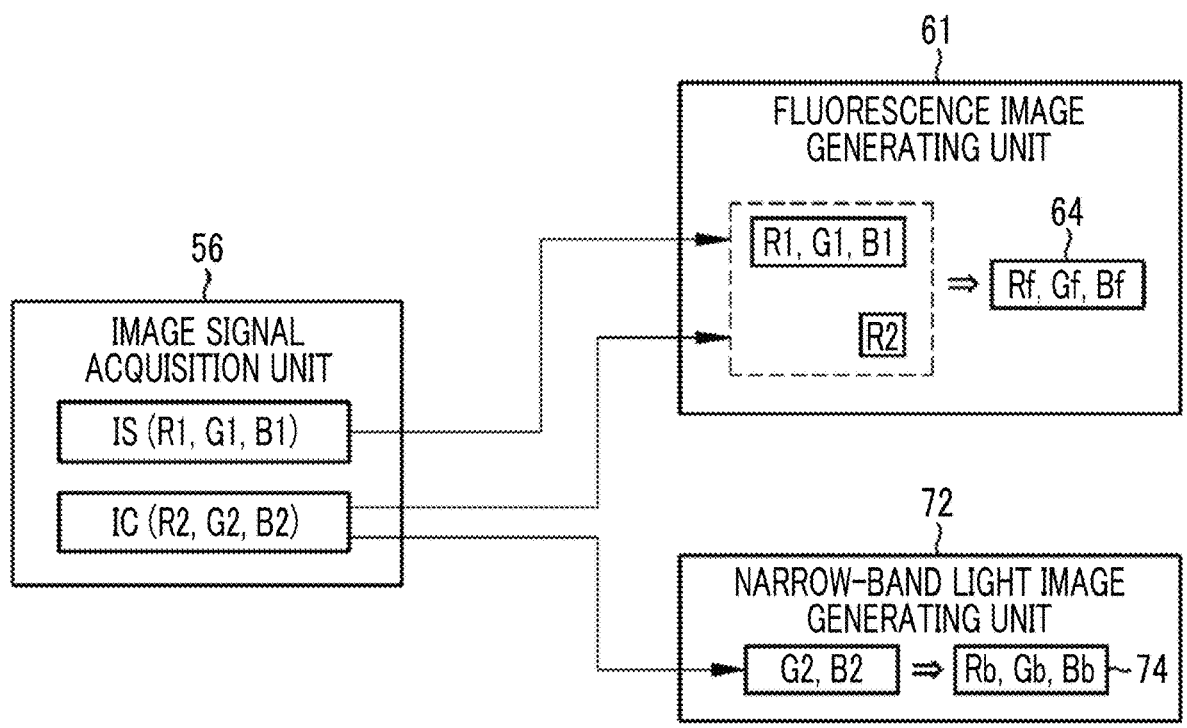
FIG. 20 is a diagram illustrating an example of the generation of a fluorescence image performed by a fluorescence image generating unit and the generation of a narrow-band light image performed by a narrow-band light image generating unit.

FIG. 20 is a diagram illustrating an example of the generation of the fluorescence image 64 performed by the fluorescence image generating unit 61 and the generation of the narrow-band light image 74 performed by the narrow-band light image generating unit 72. As shown in FIG. 20, the reflected light-image pickup signal IS includes a signal component R1 that is acquired by a red pixel 53 of the image pickup element 49, a signal component G1 that is acquired by a green pixel 53, and a signal component B1 that is acquired by a blue pixel 53. Further, the resultant light-image pickup signal IC includes a signal component R2 that is acquired by a red pixel 53 of the image pickup element 49, a signal component G2 that is acquired by a green pixel 53, and a signal component B2 that is acquired by a blue pixel 53.

The fluorescence image generating unit 61 generates the already-described simple fluorescence image 64a on the basis of the signal component R2 of the resultant light-image pickup signal IC acquired from the image signal acquisition unit 56, that is, the signal component R2 that is obtained from the image pickup using red fluorescence FL performed by a red pixel 53. Further, the fluorescence image generating unit 61 generates the already-described background image 64b on the basis of the signal components R1, G1, and B1 of the reflected light-image pickup signal IS acquired from the image signal acquisition unit 56. Then, the fluorescence image generating unit 61 combines the simple fluorescence image 64a (the signal component R2) with the background image 64b (the signal components R1, G1, and B1) to generate signal components Rf, Gf, and Bf that are to be output to RGB channels (not shown) of the monitor 13. Accordingly, the fluorescence image 64, which is formed of the signal components Rf, Gf, and Bf, is generated and is sequentially output to the display control unit 58 and the storage unit 59 from the fluorescence image generating unit 61.

The narrow-band light image generating unit 72 performs pseudo coloring, that is, generates signal components Rb, Gb, and Bb, which are to be output to RGB channels (not shown) of the monitor 13, on the basis of the signal components G2 and B2 of the resultant light-image pickup signal IC acquired from the image signal acquisition unit 56, that is, the signal components G2 and B2 that are obtained from the image pickup using the image light of the surface-layer blood vessel image and the image light of the middle-layer blood vessel image of the portion 34 to be observed performed by green and blue pixels 53. Since a specific method of generating the signal components Rb, Gb, and Bb is a publicly known technique, the detailed description thereof will be omitted here. Accordingly, the narrow-band light image 74, which is formed of the signal components Rb, Gb, and Bb, is generated and is sequentially output to the display control unit 58 and the storage unit 59 from the narrow-band light image generating unit 72.

Returning to FIG. 17, the display control unit 58 of the third embodiment sequentially outputs the observation image 63, the fluorescence image 64, and the narrow-band light image 74, which are sequentially input from the observation image generating unit 60, the fluorescence image generating unit 61, and the narrow-band light image generating unit 72, respectively, to the monitor 13 to make the monitor 13 simultaneously display the respective images or alternately display the respective images while shifting the time. A specific display method is not particularly limited. Further, the storage unit 59 of the third embodiment stores the observation image 63, the fluorescence image 64, and the narrow-band light image 74 that are sequentially input from the observation image generating unit 60, the fluorescence image generating unit 61, and the narrow-band light image generating unit 72, respectively. Accordingly, a multi-frame function is realized even in the third embodiment.

As described above, green narrow-band excitation light ELx where the transmittance of a red color filter 54R (second color filter) is low is used for not only fluorescence observation but also narrow-band light observation in the third embodiment, so that the narrow-band light image 74 can be acquired and the good fluorescence image 64 can be acquired. As a result, all of the normal observation, the fluorescence observation, and the narrow-band light observation can be performed by a simple configuration.

Fourth Embodiment

An endoscope apparatus 9B of a fourth embodiment of the invention will be described. The endoscope apparatus 9A of the third embodiment performs the normal observation, the fluorescence observation, and the narrow-band light observation. In contrast, the endoscope apparatus 9B of the fourth embodiment performs oxygen saturation observation for acquiring and observing an oxygen saturation image 80, which displays oxygen saturation so that oxygen saturation can be recognized, in addition to the normal observation, the fluorescence observation, and the narrow-band light observation. In the fourth embodiment, fluorescein and the like are used as the fluorescent dye 33.

Figure 21:
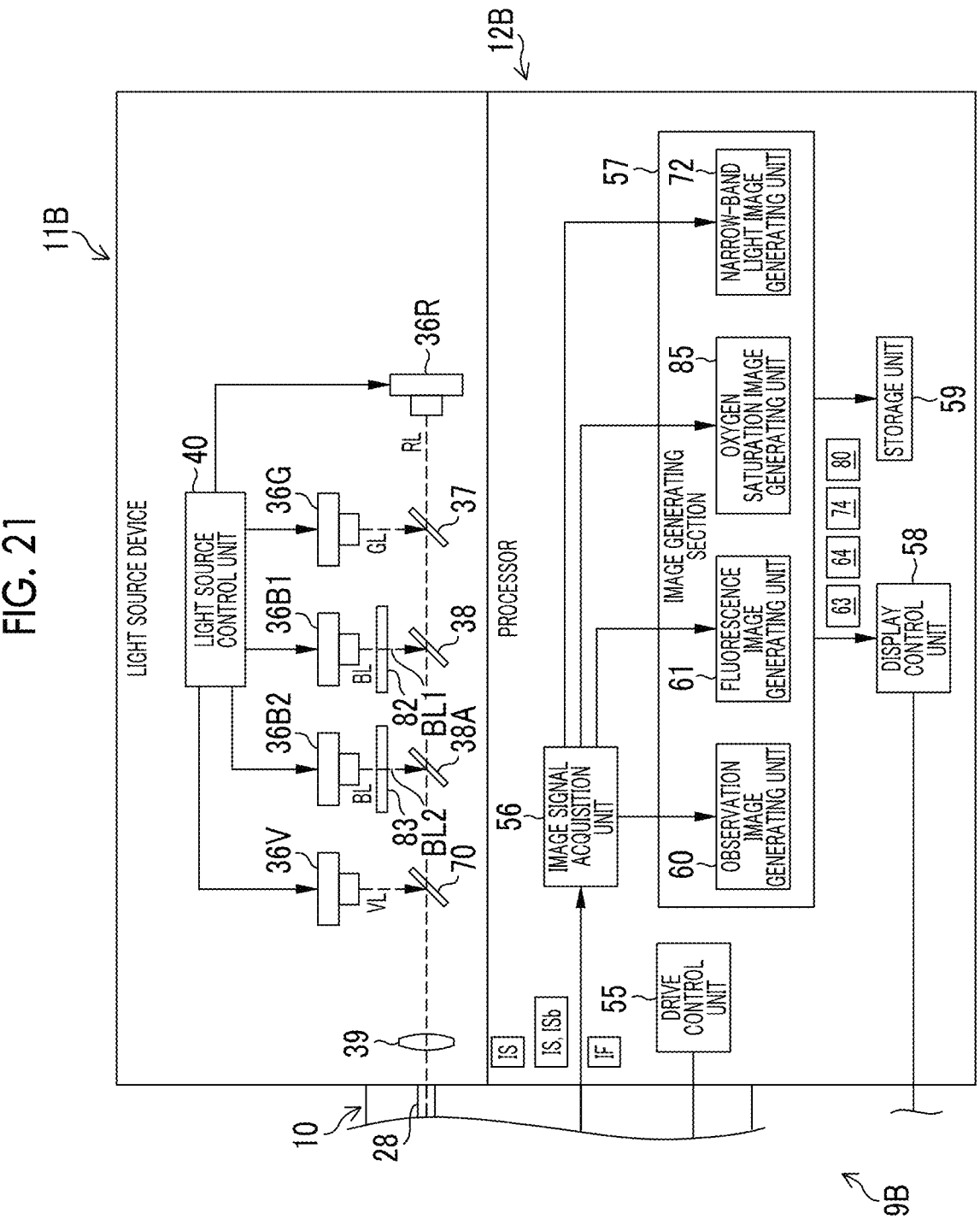
FIG. 21 is a block diagram showing the configuration of an endoscope apparatus of a fourth embodiment.

FIG. 21 is a block diagram showing the configuration of the endoscope apparatus 9B of the fourth embodiment. The endoscope apparatus 9B has four types of observation modes including an oxygen saturation observation mode in which oxygen saturation observation is performed in addition to a normal observation mode in which the already-described normal observation is performed, a fluorescence observation mode in which the fluorescence observation is performed, and a narrow-band light observation mode in which the narrow-band light observation is performed.

As shown in FIG. 21, the configuration of the endoscope apparatus 9B is basically the same as the configurations of the endoscope apparatuses 9 and 9A of the respective embodiments except that the endoscope apparatus 9B includes a light source device 11B and a processor 12B different from the light source device and the processor of each of the above-mentioned embodiments. For this reason, components having the same functions and configurations as those of each of the above-mentioned embodiments will be denoted by the same reference numerals as the reference numerals of each of the above-mentioned embodiments, and the description thereof will be omitted.

The configuration of the light source device 11B is basically the same as the configuration of the light source device 11A of the third embodiment shown in already-described FIG. 17 except that the light source device 11B includes two types of semiconductor light sources 36B1 and 36B2 provided between the semiconductor light source 36G and the semiconductor light source 36V, a long-wavelength cut filter 82, a short-wavelength cut filter 83, and a dichroic filter 38A.

The long-wavelength cut filter 82 is disposed on the optical path of blue light BL emitted from a semiconductor light source 36B1, and forms a second semiconductor light source of the invention together with the semiconductor light source 36B1. The short-wavelength cut filter 83 is disposed on the optical path of blue light BL emitted from a semiconductor light source 36B2, and forms a third semiconductor light source of the invention together with the semiconductor light source 36B2. The semiconductor light source 36V corresponds to a first semiconductor light source of the invention.

Figure 22:
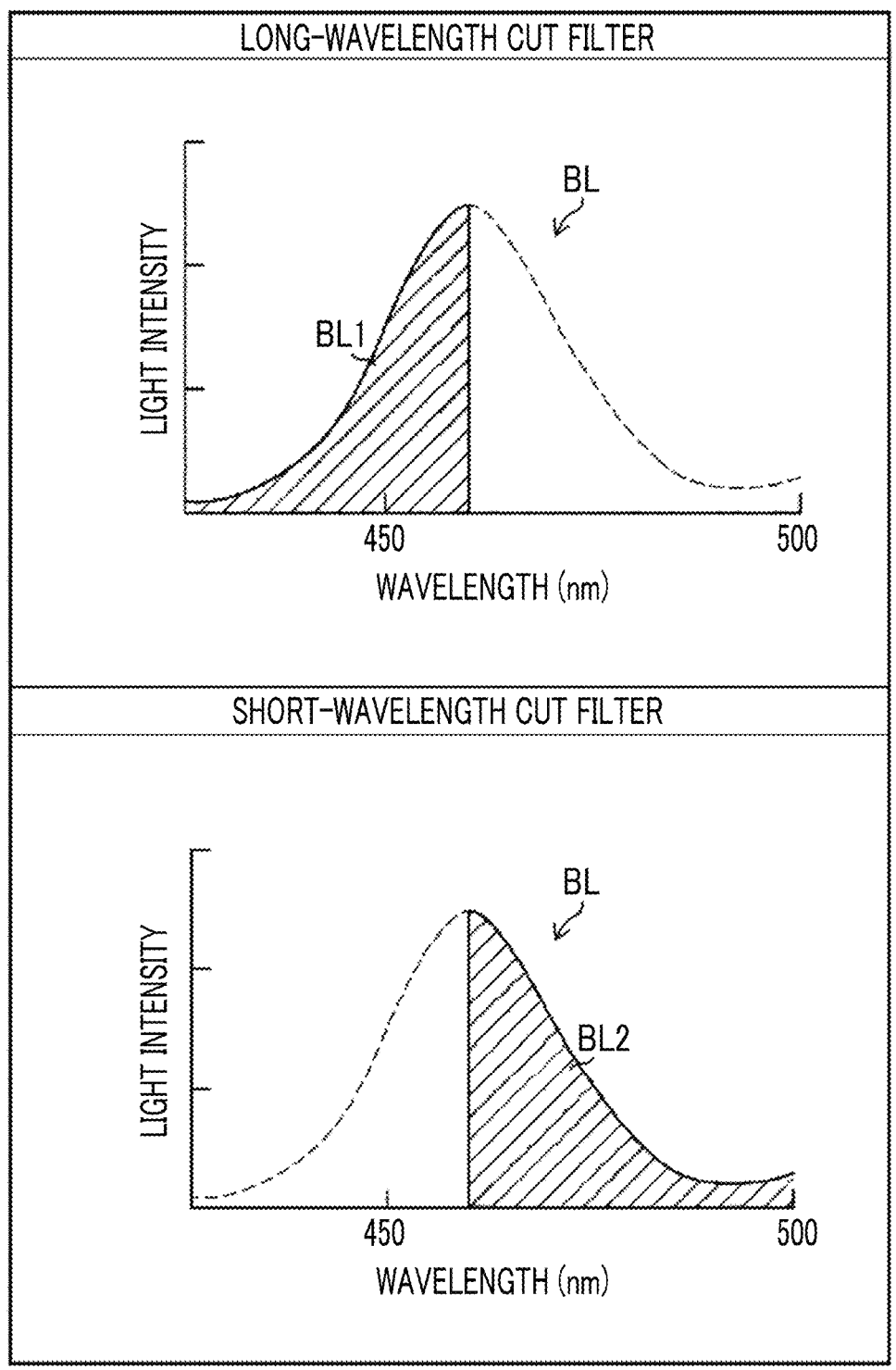
FIG. 22 is a diagram illustrating light transmitted through a long-wavelength cut filter and light transmitted through a short-wavelength cut filter.

FIG. 22 is a diagram illustrating light transmitted through the long-wavelength cut filter 82 and light transmitted through the short-wavelength cut filter 83. As shown in the upper stage of FIG. 22, the long-wavelength cut filter 82 transmits first blue light BL1 of a short wavelength-side wavelength region that is obtained in a case in which a wavelength region corresponding to a wavelength longer than a predetermined wavelength (for example, a center wavelength) is cut out of the wavelength region of blue light BL. Further, as shown in the lower stage of FIG. 22, the short-wavelength cut filter 83 transmits second blue light BL2 of a long wavelength-side wavelength region that is obtained in a case in which a wavelength region corresponding to a wavelength shorter than the predetermined wavelength is cut out of the wavelength region of blue light BL.

Returning to FIG. 21, the first blue light BL1 transmitted through the long-wavelength cut filter 82 is reflected by the dichroic filter 38 and is incident on the dichroic filter 38A together with red light RL and green light GL having been already described.

The dichroic filter 38A is disposed at an intersection between the optical path of the second blue light BL2 transmitted through the short-wavelength cut filter 83 and the optical path of red light RL. The dichroic filter 38A transmits the red light RL, the green light GL, and the first blue light BL1, which are incident from the dichroic filter 38, and reflects the second blue light BL2, which is incident from the short-wavelength cut filter 83, to the dichroic filter 70.

The wavelength limiting filter 68 (see FIG. 17) is removably disposed on the optical path of the green light GL emitted from the semiconductor light source 36G as in the third embodiment and the wavelength limiting filter 68 may be inserted onto the optical path of the green light GL in the narrow-band light observation mode.

Figure 23:
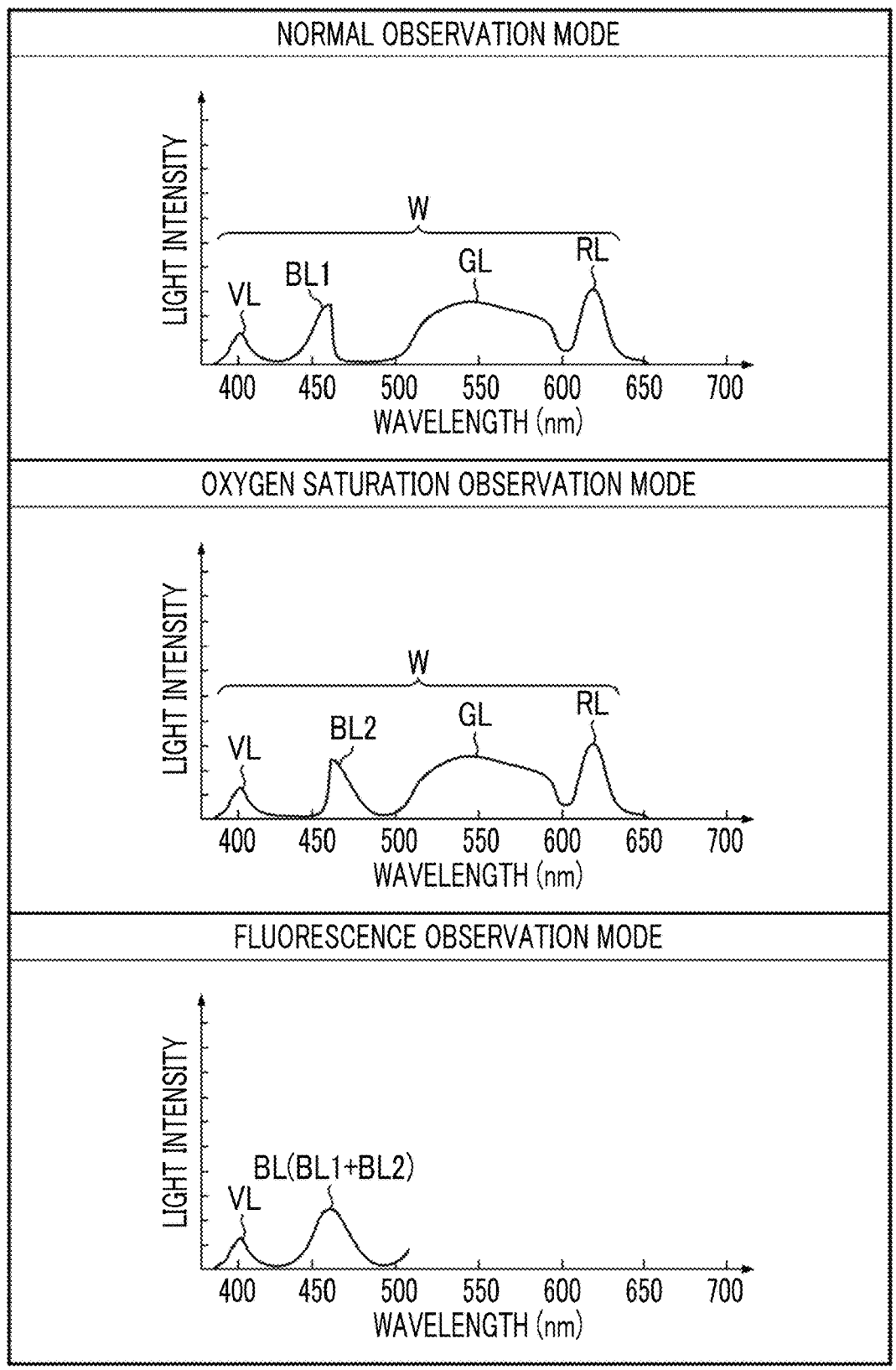
FIG. 23 is graphs showing examples of the spectral characteristics of respective color lights emitted from a light source device in the respective observation modes of the fourth embodiment.

FIG. 23 is graphs showing examples of the spectral characteristics of the respective color lights emitted from the light source device 11B in the respective observation modes of the fourth embodiment.

As shown in FIG. 23, the light source control unit 40 of the fourth embodiment simultaneously operates the respective semiconductor light sources 36R, 36G, 36B1, and 36V except for the semiconductor light source 36B2 in the normal observation mode. Accordingly, white light W including red light RL, green light GL, first blue light BL1, and purple light VL is emitted from the light source device 11B, and is applied to the portion 34 to be observed through the light guide 28 and the like of the endoscope 10. Then, an image is picked up using reflected light WR (see FIG. 17) of the white light W reflected from the portion 34 to be observed by the image pickup element 49 of the endoscope 10, and a reflected light-image pickup signal IS is output to the processor 12B.

Although not shown, the light source control unit 40 of the fourth embodiment operates any one of or both of the semiconductor light sources 36B1 and 36V in the narrow-band light observation mode. Accordingly, the first blue light BL1 or the purple light VL, which is narrow-band light, is emitted from the light source device 11B and is applied to the portion 34 to be observed through the light guide 28 and the like of the endoscope 10. Then, an image is picked up using reflected light VR (see FIG. 17) reflected from the portion 34 to be observed by the image pickup element 49 of the endoscope 10, and a reflected light-image pickup signal (not shown) is output to the processor 12B.

In this case, as in the already-described third embodiment, the portion 34 to be observed may be irradiated with the narrow-band green light GLx by the wavelength limiting filter 68 and an image may be picked up using the reflected light GR (see FIG. 17) of the narrow-band green light GLx by the image pickup element 49.

As shown in the middle stage of FIG. 23, the light source control unit 40 of the fourth embodiment switches the operation of the respective semiconductor light sources 36R, 36G, 36B2, and 36V except for the semiconductor light source 36B1 and the operation of only the semiconductor light source 36B2 in the oxygen saturation observation mode corresponding to a special emission mode of the invention. Accordingly, white light W, which includes red light RL, green light GL, second blue light BL2, and purple light VL, and the second blue light BL2 are emitted from the light source device 11B while being switched, and are applied to the portion 34 to be observed through the light guide 28 and the like of the endoscope 10.

Further, an image is picked up using the reflected light WR (see FIG. 17) of the white light W reflected from the portion 34 to be observed by the image pickup element 49 of the endoscope 10, and an image is picked up using reflected light (not shown) of the second blue light BL2 by the image pickup element 49 of the endoscope 10. Accordingly, a reflected light-image pickup signal IS of the reflected light WR and a blue reflected light-image pickup signal ISb (see FIG. 21), which is obtained from the image pickup using the reflected light of the second blue light BL2, are output to the processor 12B.

As shown in the lower stage of FIG. 23, the light source control unit 40 of the fourth embodiment operates the semiconductor light sources 36B1 and 36B2 or operates the semiconductor light sources 36B1, 36B2, and 36V in the fluorescence observation mode. Accordingly, blue light BL (first blue light BL1+second blue light BL2) is emitted from the light source device 11B or blue light BL and purple light VL are emitted from the light source device 11B as excitation light EL, and are applied to the portion 34 to be observed through the light guide 28 and the like of the endoscope 10. Therefore, in a case in which the light source control unit 40 operates the semiconductor light sources 36B1, 36B2, and 36V, the portion 34 to be observed is irradiated with three types of excitation light EL that are included in a wavelength region corresponding to a bluish color including purple and blue and have peak wavelengths different from each other. The three types of excitation light EL are also absorbed in the fluorescent dye, so that the intensity of fluorescence is increased. The number of the types of excitation light EL is not limited to three, and three or more types of excitation light EL included in a wavelength region corresponding to a bluish color may be provided.

Then, the fluorescent dye 33 contained in the portion 34 to be observed is excited by the excitation light EL so as to emit light, fluorescence FL (see FIG. 17) is generated, an image is picked up using the fluorescence FL by the image pickup element 49 of the endoscope 10, and a fluorescence-image pickup signal IF (see FIGS. 2 and 21) is output to the processor 12B.

Since the background image 64b generated on the basis of the reflected light-image pickup signal IS is necessary for the generation of the fluorescence image 64 as already described, the light source control unit 40 of the fourth embodiment makes white light W be emitted from the light source device 11B in the fluorescence observation mode as in the already-described first embodiment. Accordingly, a reflected light-image pickup signal IS is output to the processor 12B even in the fluorescence observation mode.

Returning to FIG. 21, the configuration of the processor 12B is basically the same as the configuration of the processor 12A (see FIG. 17) of the third embodiment except that the image generating section 57 functions as an oxygen saturation image generating unit 85 in addition to the observation image generating unit 60, the fluorescence image generating unit 61, and the narrow-band light image generating unit 72 having been already described.

The observation image generating unit 60 of the fourth embodiment generates an observation image 63 on the basis of a reflected light-image pickup signal IS acquired from the image signal acquisition unit 56 in the normal observation mode as in the above-mentioned first embodiment. Further, the fluorescence image generating unit 61 generates a fluorescence image 64 on the basis of a fluorescence-image pickup signal IF and a reflected light-image pickup signal IS acquired from the image signal acquisition unit 56 in the fluorescence observation mode as in the above-mentioned first embodiment. Furthermore, the narrow-band light image generating unit 72 generates a narrow-band light image 74 on the basis of a reflected light-image pickup signal (not shown), which is obtained from the image pickup using reflected light VR, or a reflected light-image pickup signal (not shown), which is obtained from the image pickup using reflected light VR and reflected light GR as in the above-mentioned third embodiment, in the narrow-band light observation mode.

In the oxygen saturation observation mode, the oxygen saturation image generating unit 85 calculates the oxygen saturation of the portion 34 to be observed on the basis of the blue reflected light-image pickup signal ISb acquired from the image signal acquisition unit 56 and generates the oxygen saturation image 80, which represents the oxygen saturation of the portion 34 to be observed, on the basis of the result of calculation of the oxygen saturation and the reflected light-image pickup signal IS acquired from the image signal acquisition unit 56. Since a specific method of generating the oxygen saturation image 80 is a publicly known technique, the detailed description thereof will be omitted here.

The observation image 63, the fluorescence image 64, the narrow-band light image 74, and the oxygen saturation image 80, which are generated in the respective observation modes, are output to the display control unit 58 and the storage unit 59, are displayed on the monitor 13, and are stored in the storage unit 59.

Figure 24:
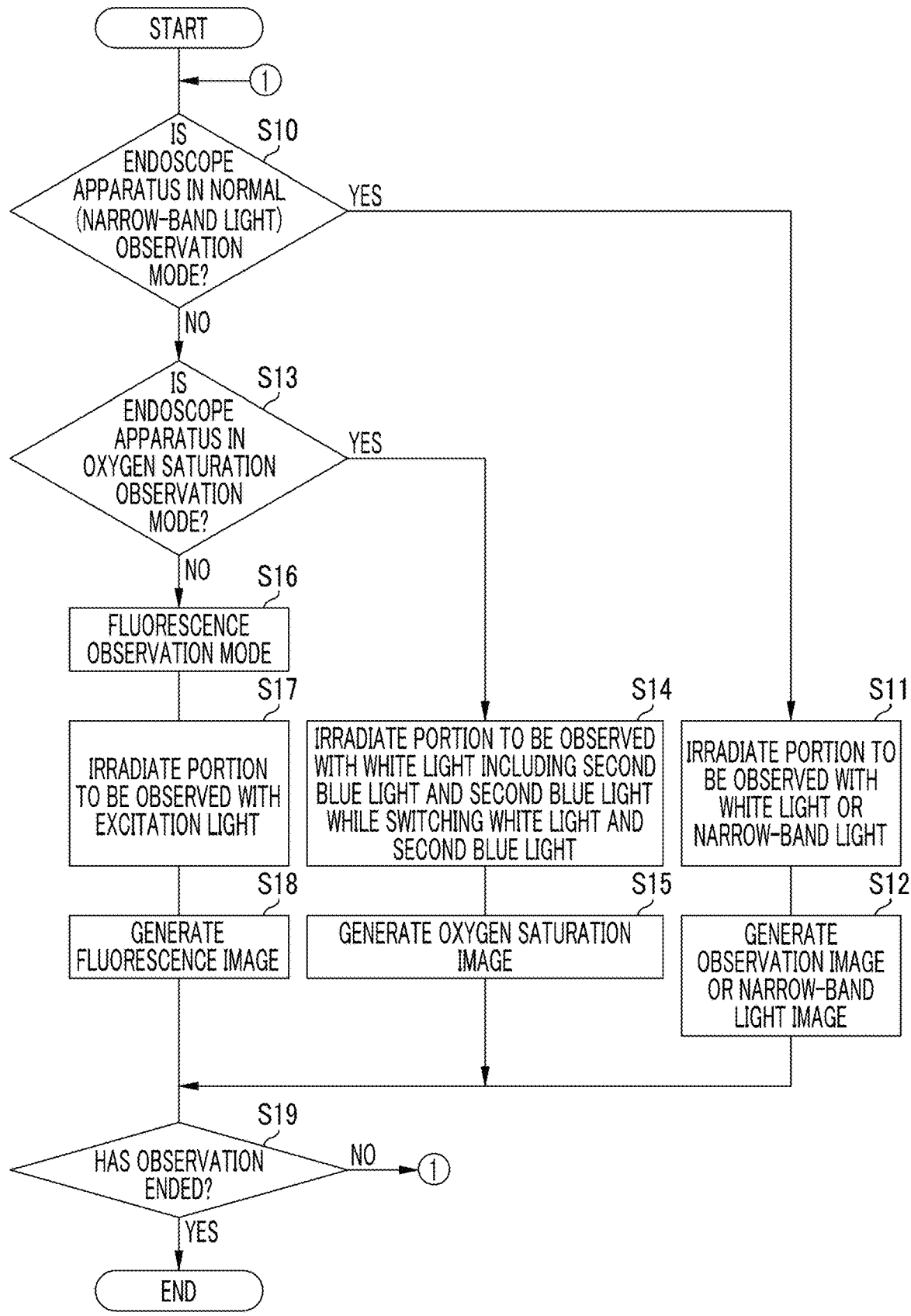
FIG. 24 is a flow chart showing an example of the flow of processing in each observation mode that is performed by the endoscope apparatus of the fourth embodiment.

FIG. 24 is a flow chart showing an example of the flow of processing in each observation mode that is performed by the endoscope apparatus 9B of the fourth embodiment. As shown in FIG. 24, if the endoscope apparatus 9B is in the normal observation mode (YES in Step S10), white light W including red light RL, green light GL, first blue light BL1, and purple light VL is emitted from the light source device 11B under the control of the light source control unit 40 (see the upper stage of FIG. 22) and a portion 34 to be observed is irradiated with the white light W (Step S11). Accordingly, an image is picked up using reflected light WR of the white light W, which is reflected from the portion 34 to be observed, by the image pickup element 49 of the endoscope 10 and a reflected light-image pickup signal IS is output to the processor 12B. Then, an observation image 63 is generated by the observation image generating unit 60 of the processor 12B, and the observation image 63 is displayed on the monitor 13 by the display control unit 58 and is stored in the storage unit 59 (Step S12).

Further, if the endoscope apparatus 9B is in the narrow-band light observation mode (YES in Step S10), first blue light BL1 or purple light VL, which is narrow-band light, (and narrow-band green light GLx as necessary) is emitted from the light source device 11B under the control of the light source control unit 40 and a portion 34 to be observed is irradiated with the narrow-band light (Step S11). Accordingly, an image is picked up using reflected light (not shown) of the narrow-band light, which is reflected from the portion 34 to be observed, by the image pickup element 49 of the endoscope 10 and a reflected light-image pickup signal (not shown) is output to the processor 12B. Then, a narrow-band light image 74 is generated by the narrow-band light image generating unit 72 of the processor 12B, and the narrow-band light image 74 is displayed on the monitor 13 by the display control unit 58 and is stored in the storage unit 59 (Step S12).

Furthermore, if the endoscope apparatus 9B is in the oxygen saturation observation mode (NO in Step S10, YES in Step S13), white light W, which includes red light RL, green light GL, second blue light BL2, and purple light VL, and the second blue light BL2 are emitted from the light source device 11B under the control of the light source control unit 40 while being switched (see the middle stage of FIG. 22), and are applied to the portion 34 to be observed (Step S14). Accordingly, images are picked up using reflected light WR of the white light W and reflected light (not shown) of the second blue light BL2 by the image pickup element 49 of the endoscope 10, and a reflected light-image pickup signal IS and a blue reflected light-image pickup signal ISb are output to the processor 12B. Then, an oxygen saturation image 80 is generated by the oxygen saturation image generating unit 85 of the processor 12B, and the oxygen saturation image 80 is displayed on the monitor 13 by the display control unit 58 and is stored in the storage unit 59 (Step S15).

Moreover, if the endoscope apparatus 9B is in the fluorescence observation mode (NO in Steps S10 and S13, Step S16), blue light BL or blue light BL and purple light VL are emitted from the light source device 11B as excitation light EL under the control of the light source control unit 40 and a portion 34 to be observed is irradiated with the excitation light EL (Step S17). Accordingly, an image is picked up using fluorescence FL generated from the fluorescent dye 33 of the portion 34 to be observed by the image pickup element 49 of the endoscope 10 and a fluorescence-image pickup signal IF is output to the processor 12B. The emission of the white light W from the light source device 11B, the image pickup using the reflected light WR, and the output of the reflected light-image pickup signal IS to the processor 12B are performed as in the already-described first embodiment. Then, a fluorescence image 64 is generated by the fluorescence image generating unit 61 of the processor 12B, and the fluorescence image 64 is displayed on the monitor 13 by the display control unit 58 and is stored in the storage unit 59 (Step S18).

The processing of the above-mentioned respective steps are repeatedly performed until observation performed by the endoscope apparatus 9B ends (Step S19).

The respective observation modes of the endoscope apparatus 9B may be continuously and repeatedly performed. Accordingly, a multi-frame function to simultaneously display the respective images on the monitor 13 or to display the respective images on the monitor 13 while switching the respective images and to store the respective images in the storage unit 59 is realized even in the fourth embodiment.

Since the first blue light BL1 and the second blue light BL2 can be selectively emitted from the light source device 11B as described above in the endoscope apparatus 9B of the fourth embodiment, the oxygen saturation observation mode can be performed in addition to the normal observation mode, the fluorescence observation mode, and the narrow-band light observation mode. Further, since two types of semiconductor light sources 36B1 and 36B2, the long-wavelength cut filter 82, and the short-wavelength cut filter 83 may be disposed in the light source device 11B, which relatively has an extra arrangement space therein, to be capable of selectively emitting the first blue light BL1 and the second blue light BL2, each observation can be realized by a simple configuration.

The light source device 11B is provided with five types of semiconductor light sources 36R, 36G, 36B1, 36B2, and 36V in total in the fourth embodiment, but may be provided with four types of light sources except for the semiconductor light source 36R.

EXAMPLES

Examples (Comparative Examples) of the invention will be described below to specifically describe the invention. However, the invention is not limited to these examples (Comparative Examples). Among Examples 1 to 27, Examples 6, 7, 9 to 11, 24, and 26 are Comparative Examples.

Figure 25:
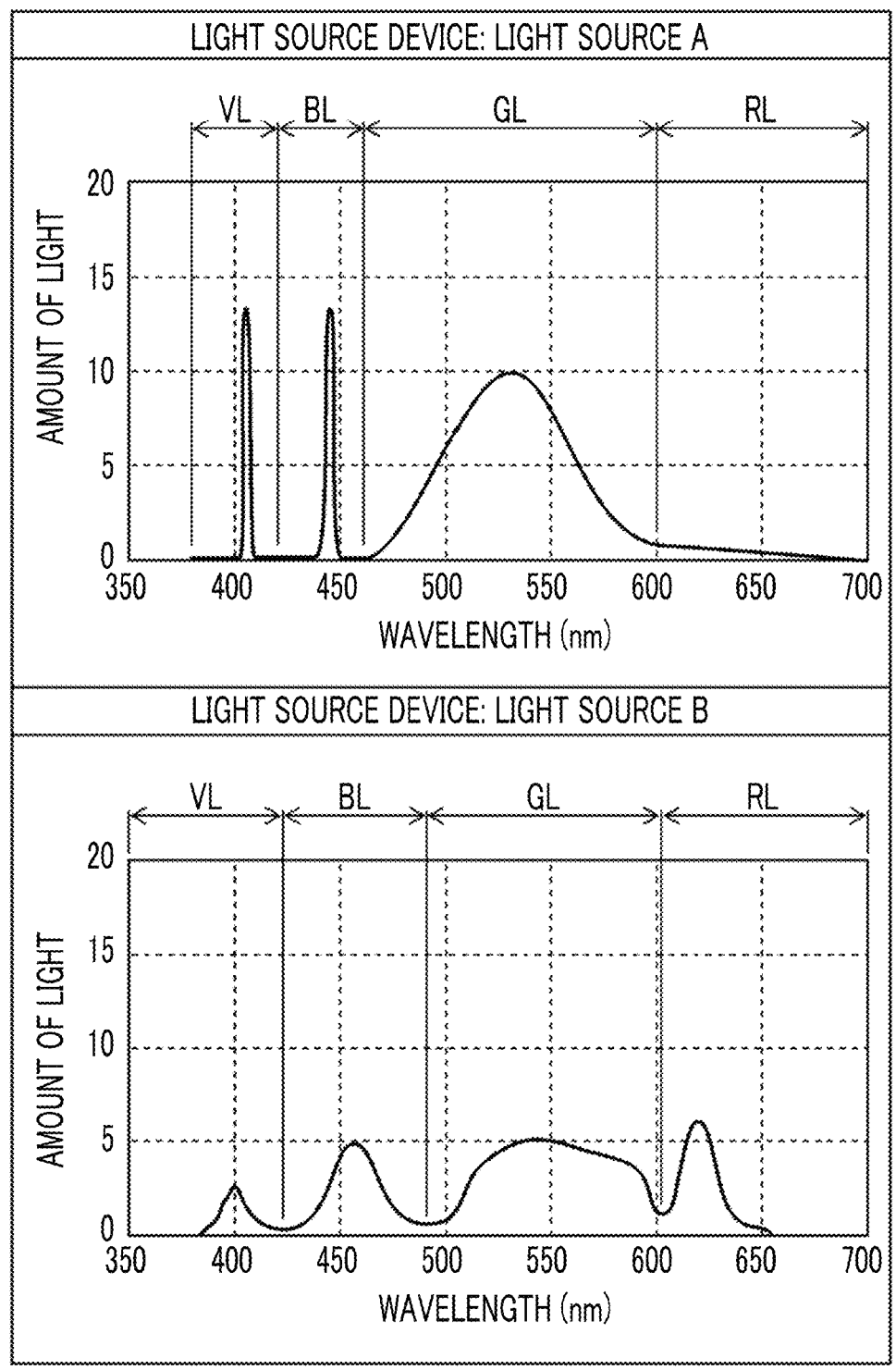
FIG. 25 is graphs showing the spectral characteristics of light emitted from light source devices used in the respective examples.
Figure 26:
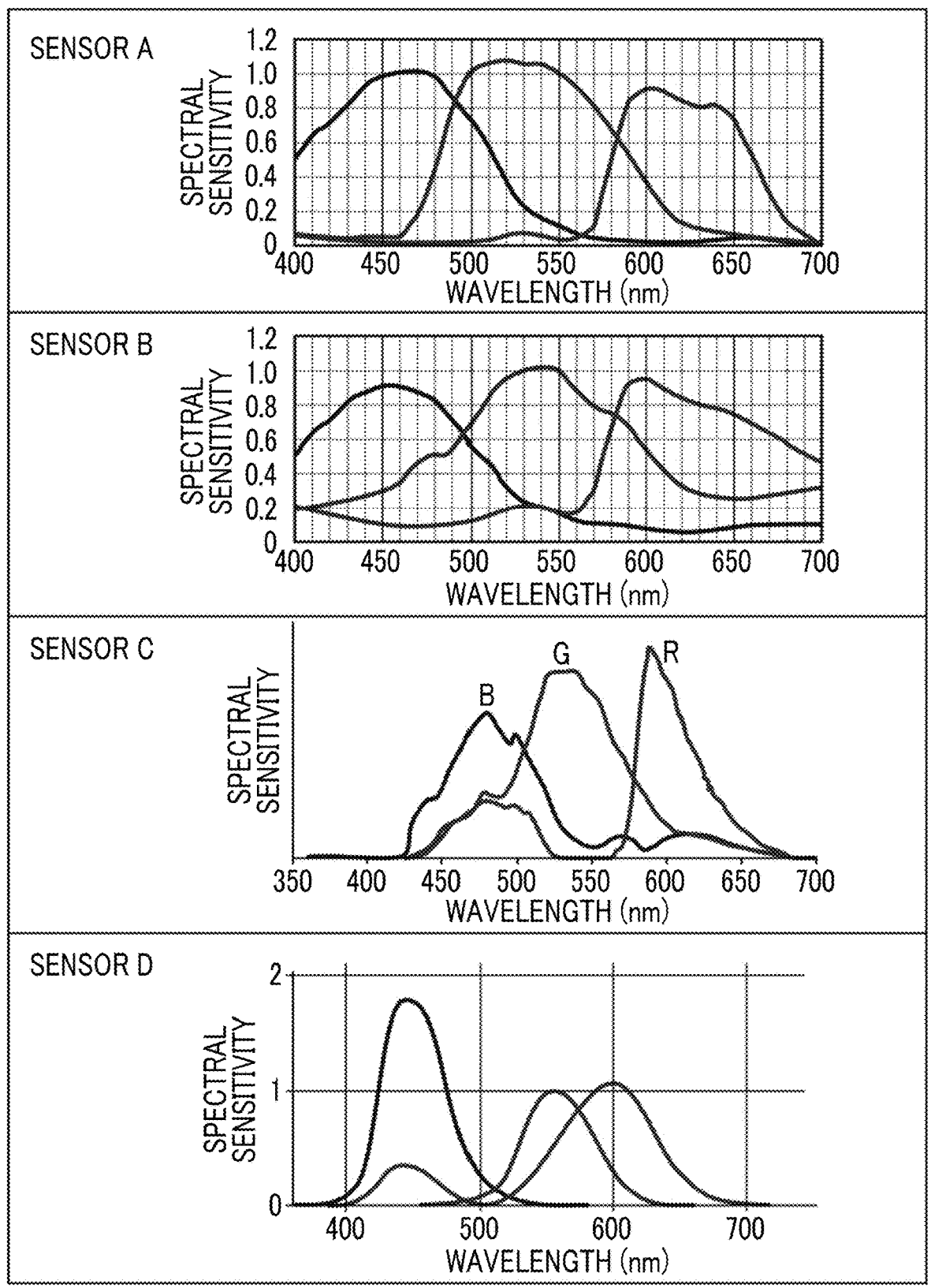
FIG. 26 is graphs substantially showing the spectral sensitivities of the respective pixels of image pickup elements used in the respective examples, that is, the spectral transmittance characteristics of color filters.
Figure 27:
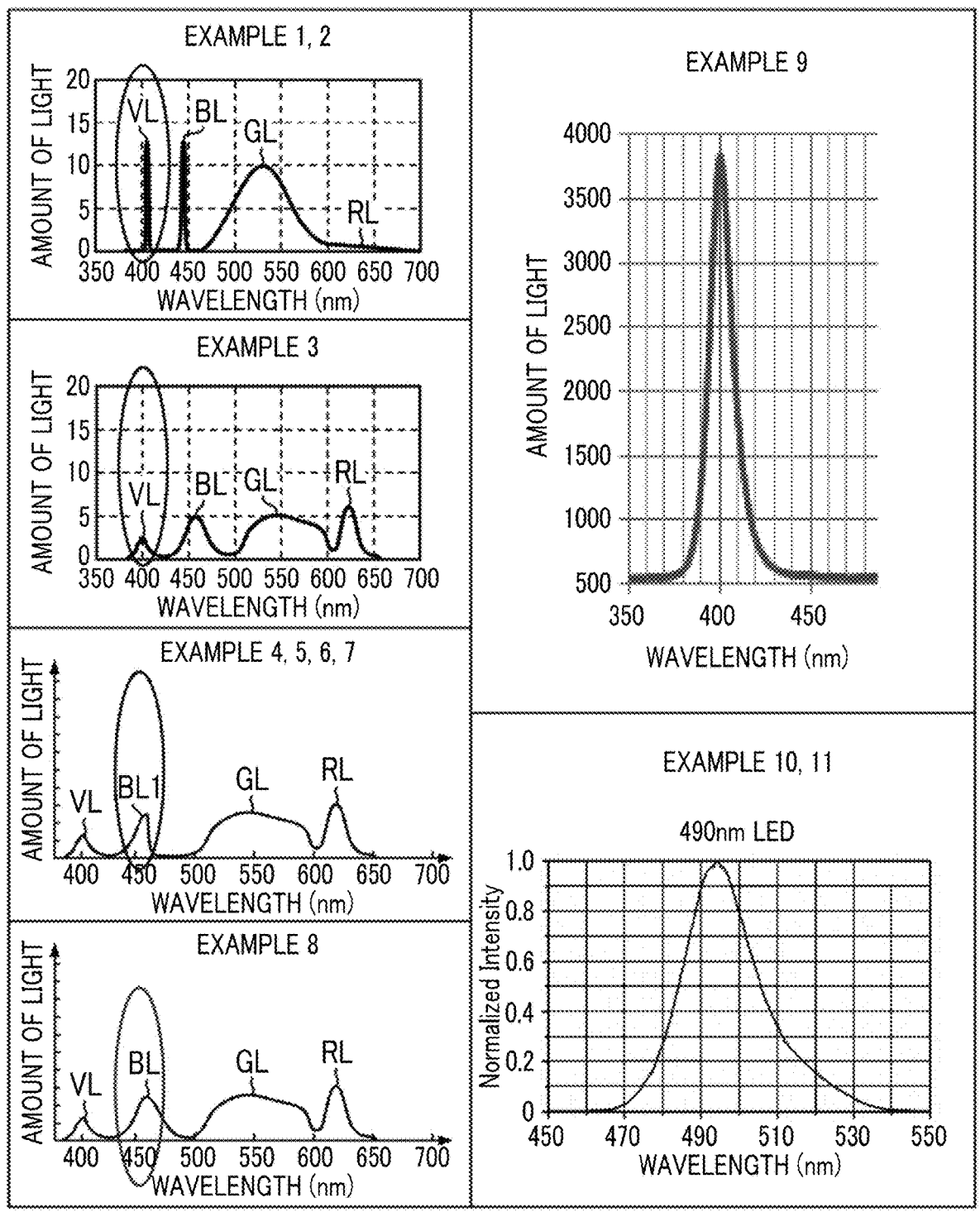
FIG. 27 is a diagram illustrating the wavelength regions of excitation lights emitted from the light source devices in Examples 1 to 11 (the same applies to Examples 12 to 22).
Figure 28:
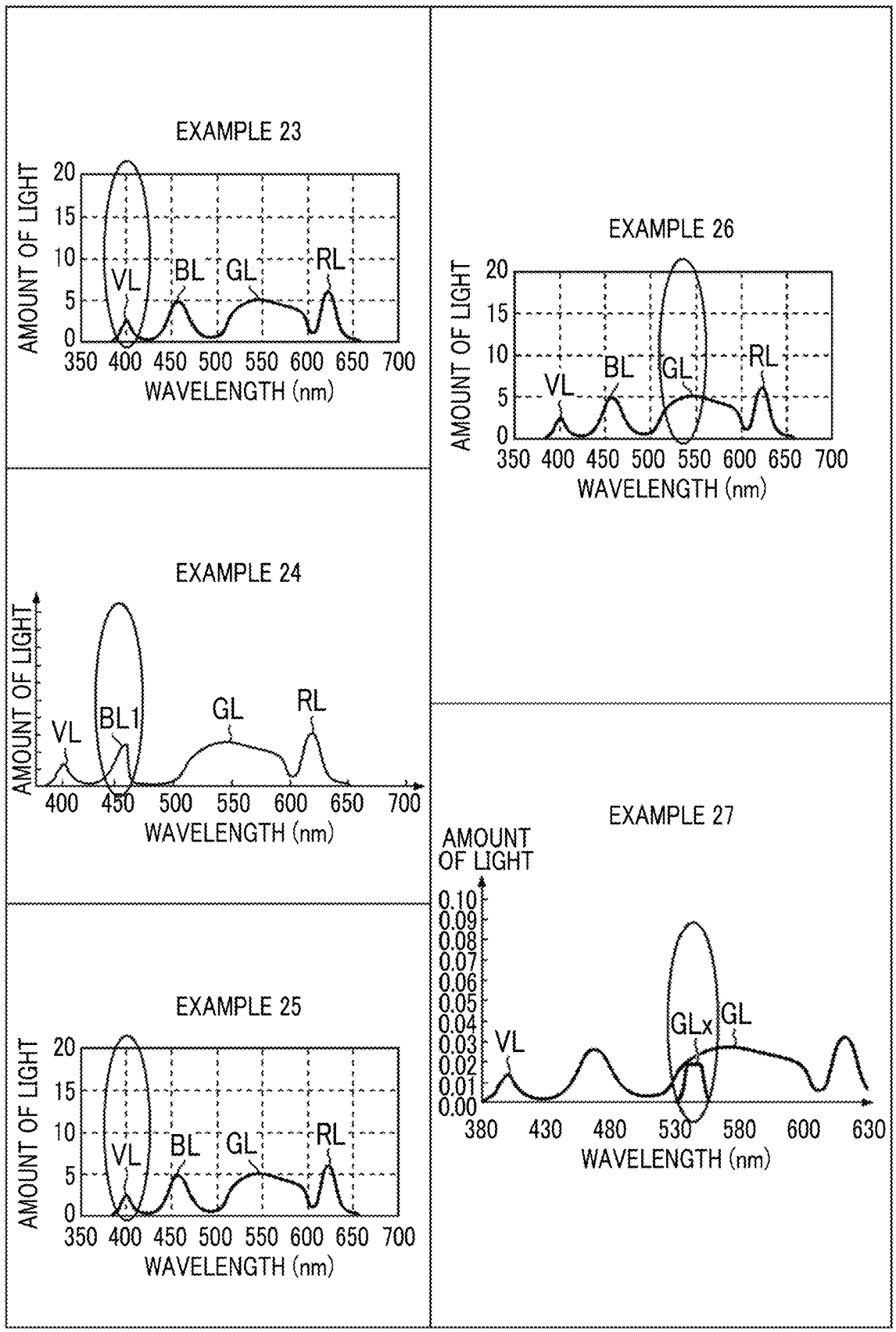
FIG. 28 is a diagram illustrating the wavelength regions of excitation lights emitted from light source devices in Examples 23 to 27.

FIG. 25 is graphs showing the spectral characteristics of light emitted from light source devices 11 used in the respective examples. FIG. 26 is graphs substantially showing the spectral sensitivities of the respective pixels 53 of image pickup elements 49 used in the respective examples, that is, the spectral transmittance characteristics of color filters 54. FIG. 27 is a diagram illustrating the wavelength regions of excitation lights EL emitted from the light source devices 11 in Examples 1 to 11 (the same applies to Examples 12 to 22). Further, FIG. 28 is a diagram illustrating the wavelength regions of excitation lights EL emitted from light source devices 11 in Examples 23 to 27.

In the respective examples, a "light source A" that is a laser light source having a spectral characteristic shown in the upper stage of FIG. 25 and a "light source B" that is an LED light source having a spectral characteristic shown in the lower stage of FIG. 25 were used as the light source device 11 (see FIGS. 29 and 30 to be described later). As shown in FIGS. 29 and 30 to be described later, the "light source A" emits PDD light used for photodynamic diagnosis (PDD). The "light source B" emits purple light (V light) and blue light (B light) [including first blue light BL1 (BL1 light) and second blue light BL2 (BL2 light)], and the like.

Further, an LED light source emitting excitation light EL having a center wavelength of 400 nm was used in Example 9, and an LED light source emitting excitation light EL having a center wavelength of 490 nm was used in Examples 10 and 11 (see FIGS. 29 and 30 to be described later). Furthermore, a GLED light source emitting green light (G light) having a wavelength region of 520 to 550 nm as excitation light EL was used in Examples 26 and 27 (see FIGS. 29 and 30 to be described later). Moreover, a wavelength limiting filter 68 (a "filter" of FIG. 30) shown in already-described FIG. 15 was provided in Example 27 so that narrow-band green light GLx (narrow-band excitation light ELx: see FIG. 16) was emitted.

A "sensor A", a "sensor B", a "sensor C", and a "sensor D" having the spectral characteristics shown in FIG. 26 were used in the respective examples as the image pickup elements 49 (see FIGS. 29 and 30 to be described later).

In the respective examples, portions 34 to be observed were irradiated with excitation lights EL of wavelength regions shown in FIGS. 27 and 28 as the excitation lights EL (see FIGS. 29 and 30 to be described later). Since the excitation lights EL used in Examples 12 to 22 are the same as the excitation lights EL used in Examples 1 to 11, the excitation lights EL used in Examples 12 to 22 are not shown in FIG. 28. Further, the peak wavelengths of the respective excitation lights EL are described in FIGS. 29 and 30.

Fluorescein having the absorption spectrum and the fluorescence spectrum shown in already-described FIG. 7 was used as a fluorescent dye 33 in each of Examples 1 to 11. Furthermore, Rhodamine Green having the absorption spectrum and the fluorescence spectrum shown in already-described FIG. 10 was used as a fluorescent dye 33 in each of Examples 12 to 22. In addition, PpIX having the absorption spectrum shown in already-described FIG. 11 was used as a fluorescent dye 33 in Examples 23 to 25. Moreover, SYPRO Red having the absorption spectrum shown in already-described FIG. 13 was used as a fluorescent dye 33 in each of Examples 26 and 27.

FIG. 29 is a diagram illustrating conditions and evaluation results of Examples 1 to 11. Further, FIG. 30 is a diagram illustrating conditions and evaluation results of Examples 12 to 27. Since the conditions and evaluation results of Examples 12 to 22 are the same as the conditions and evaluation results of Examples 1 to 11 shown in FIG. 29, the conditions and evaluation results of Examples 12 to 22 are not shown in FIG. 30.

"Condition of first wavelength region" in FIGS. 29 and 30 is a condition representing the range of the first wavelength region W1 of the absorption spectrum of the fluorescent dye 33 where the already-described first peak value P1 is used as a criterion. For example, in a case in which the "condition of first wavelength region" is 10% or more, the first wavelength region W1 is a wavelength region where the absorption intensity of the fluorescent dye 33 is 10% or more of the first peak value P1. The "condition of first wavelength region" contributes to the already-described criterion [B], that is, "fluorescence emission intensity".

"Condition of second wavelength region" is a condition representing the range of the second wavelength region W2 of the spectral transmittance characteristic (first spectral transmittance characteristic) of the color filter 54 where the already-described second peak value P2 is used as a criterion. For example, in a case in which the "condition of second wavelength region" is 60% or more, the second wavelength region W2 is a wavelength region where the transmittance of the spectral transmittance characteristic (first spectral transmittance characteristic) is 60% or more of the second peak value P2. The "condition of second wavelength region" contributes to the already-described criterion [A], that is, "sensor color separation".

"Condition of third wavelength region" is a condition representing the range of the third wavelength region W3 of the spectral transmittance characteristic (second spectral transmittance characteristic) of the color filter 54 where the already-described third peak value P3 is used as a criterion. For example, in a case in which the "condition of third wavelength region" is larger than 40% or less, the third wavelength region W3 is a wavelength region where the transmittance of the spectral transmittance characteristic (second spectral transmittance characteristic) is 40% or less of the third peak value P3. The "condition of third wavelength region" contributes to the already-described criterion [A], that is, "sensor color separation".

"Condition of fourth wavelength region" is a condition representing the range of the fourth wavelength region W4 of the spectral transmittance characteristic (second spectral transmittance characteristic) of the color filter 54 where the already-described third peak value P3 is used as a criterion. For example, in a case in which the "condition of fourth wavelength region" is 80% or more, the fourth wavelength region W4 is a wavelength region where the transmittance of the spectral transmittance characteristic (second spectral transmittance characteristic) is 80% or less of the third peak value P3. The "condition of fourth wavelength region" contributes to the already-described criterion [A], that is, "sensor color separation".

Examples 1, 3 to 5, and 8, Examples 23 and 25, and Example 27 were embodied under the condition where "condition of first wavelength region" is at least "10% or more", "condition of second wavelength region" is at least "60% or more", "condition of third wavelength region" is at least "40% or less", and "condition of fourth wavelength region" is "80% or more". These conditions are merely abbreviated as "wavelength region conditions"

On the other hand, Examples 9 and 24 as comparative examples were embodied under the condition where "condition of first wavelength region" among the "wavelength region conditions" is less than 10%. Further, Examples 2 and 6 as comparative examples were embodied under the condition where "condition of second wavelength region" among the "wavelength region conditions" is less than 60%. Furthermore, Examples 10, 11, and 26 as comparative examples were embodied under the condition where "condition of third wavelength region" among the "wavelength region conditions" is larger than 40%. In addition, Example 7 (comparative example) was embodied under the condition where "condition of fourth wavelength region" among the "wavelength region conditions" is less than 80%. The conditions of Examples 12 to 22, which are not shown in FIG. 30, are the same as the conditions of Examples 1 to 11 of FIG. 29.

"(A) Sensor color separation" corresponding to the already-described criterion [A], "(B) fluorescence emission intensity" corresponding to the already-described criterion [B], and "(C) visual performance of fluorescence image" were evaluated in each example.

The criterion of "(A) sensor color separation" is whether or not the colors of images obtained from excitation light EL and the reflected light WR of the excitation light EL and the colors of an image obtained from light emitted from the fluorescent dye 33 (fluorescent material) can be separated from each other on the image pickup element 49. For example, "(A) sensor color separation" was evaluated by both of the degree of overlap (overlap ratio) between the wavelength region of the excitation light EL and the wavelength region of the second color filter of the invention, such as the color filter 54G or 54R of the image pickup element 49 and the degree of overlap (overlap ratio) between the wavelength region of the fluorescence FL and the wavelength region of the first color filter of the invention, such as the color filter 54B of the image pickup element 49. Specifically, in this embodiment, "(A) sensor color separation" was evaluated as "fail" in a case in which the degree of overlap exceeds a predetermined upper limit, and was evaluated as "pass", "good", and "very good" in accordance with a predetermined criterion as the degree of overlap is reduced from the upper limit.

"(B) Fluorescence emission intensity" was evaluated in accordance with the emission intensity of the fluorescence FL determined by a relationship between the absorption spectrum of the fluorescent dye 33 (fluorescent material) and the spectral characteristics of the excitation light EL. Specifically, in this embodiment, "(B) fluorescence emission intensity" was evaluated as "fail" since fluorescence FL emitted from the fluorescent dye 33 is not too much in a case in which the peak of the excitation light EL overlaps only a wavelength region where the absorption spectrum of the fluorescent dye 33 is 10% or less of the peak of the absorption spectrum of the fluorescent dye 33. On the other hand, since much excitation light is absorbed by the fluorescent dye 33 in a case in which the peak of the excitation light EL overlaps a wavelength region where the absorption spectrum of the fluorescent dye 33 is 50% or more of the peak of the absorption spectrum of the fluorescent dye 33, the emission intensity of the fluorescence FL emitted from the fluorescent dye 33 is also high. For this reason, "(B) fluorescence emission intensity" was evaluated as "pass", "good", and "very good" from a relationship between the excitation light EL and the absorption spectrum of the fluorescent dye 33.

"(C) visual performance of fluorescence image" is evaluation changing in conjunction with the evaluation of "(A) sensor color separation" and "(B) fluorescence emission intensity" having been already described, and is determined depending on whether or not the fluorescent dye 33 (fluorescent material) is expressed (is estimated to be expressed) with good contrast on the image in a case in which an image is formed under the condition (evaluation) of "(A) sensor color separation" and "(B) fluorescence emission intensity". In a case in which sensor color separation is good and fluorescence emission intensity is high, the visual performance of a fluorescence image is improved. For example, in a case in which one of "(A) sensor color separation" and "(B) fluorescence emission intensity" is evaluated as "fail", "(C) visual performance of fluorescence image" is also evaluated as "fail". Further, in this embodiment, "(C) visual performance of fluorescence image" was evaluated as "fail" in accordance with a predetermined image evaluation criterion in a case in which "(C) visual performance of fluorescence image" does not satisfy the predetermined image evaluation criterion, and was evaluated as "pass", "good", and "very good" in accordance with a predetermined criterion as an image became easy to see from the image evaluation criterion.

Returning to FIGS. 29 and 30, it was confirmed that "(B) fluorescence emission intensity" was evaluated as "fail" and "(C) visual performance of fluorescence image" was evaluated as "fail" with "(B) fluorescence emission intensity" in Examples 9 and 24 as comparative examples.

Further, it was confirmed that "(A) sensor color separation" was evaluated as "fail" and "(C) visual performance of fluorescence image" was evaluated as "fail" with "(A) sensor color separation" in Examples 2, 6, 10, 11, 26, and 7 as comparative examples.

In contrast, it was confirmed that both "(A) sensor color separation" and "(B) fluorescence emission intensity" were evaluated as "pass" or more and "(C) visual performance of fluorescence image" was evaluated as "pass" with "(A) sensor color separation" and "(B) fluorescence emission intensity" in Examples 1, 3 to 5, 8, 23, 25, and 27 satisfying the "wavelength region conditions". Accordingly, it was confirmed that a good fluorescence image 64 was obtained in a case in which the "wavelength region conditions" are satisfied. The evaluation results of Examples 12 to 22, which are not shown in FIG. 30, are the same as the evaluation results of Examples 1 to 11 of FIG. 29.

Furthermore, it was confirmed from the comparison of, for example, Examples 1 and 3 and Examples 4 and 5 that the evaluation of "(B) fluorescence emission intensity" was improved in a case in which "condition of first wavelength region" is 50% or more, that is, a case in which at least a part of the wavelength region of the excitation light EL is included in the first wavelength region W1A. As a result, it was confirmed that a case in which "condition of first wavelength region" is 50% or more is more preferable than a case in which "condition of first wavelength region" is 10% or more.

In addition, it was confirmed from the comparison of Examples 3 and 5 to which, for example, "condition of third wavelength region" and "condition of fourth wavelength region" are common and of which "condition of second wavelength region" is different that the evaluation of "(A) sensor color separation" was improved in a case in which "condition of second wavelength region" is 80% or more, that is, the wavelength region of the excitation light EL is included in the second wavelength region W2A. As a result, it was confirmed that a case in which "condition of second wavelength region" is 80% or more is more preferable than a case in which "condition of second wavelength region" is 60% or more.

Moreover, it was confirmed from the comparison of Examples 4 and 8 and Example 5 to which, for example, "condition of second wavelength region" and "condition of fourth wavelength region" are common and of which "condition of third wavelength region" is different that the evaluation of "(A) sensor color separation" was improved in a case in which "condition of third wavelength region" is 20% or less, that is, the wavelength region of the excitation light EL is included in the third wavelength region W3A. As a result, it was confirmed that a case in which "condition of third wavelength region" is 20% or less is more preferable than a case in which "condition of third wavelength region" is 40% or less.

[Others]

"Fluorescein", "Rhodamine Green", "PpIX", and "SYPRO Red" have been described as the fluorescent dye 33 in the respective embodiments, but other fluorescent dyes 33 may be used. In this case, the light source device 11 and the image pickup element 49 (color filters 54) are appropriately selected so that the already-described criteria [A] and [B] are satisfied according to the type of the fluorescent dye 33. In this case, the light source device 11 may be provided with a filter that appropriately limits the wavelength region of the excitation light EL.

A case in which the fluorescent dye 33 is applied to a portion 34 to be observed has been described in each embodiment, but the fluorescent material of the invention is not limited to the fluorescent dye 33 and includes various fluorescent materials including self-fluorescent materials.

The color filters 54 of the image pickup element 49 include the red (R) color filters 54R, the green (G) color filters 54G, and the blue (B) color filters 54B in each embodiment, but may include other color filters. Further, a complementary color filter may be used as the color filter 54 in addition to a primary color filter.

A flexible endoscope has been described as an example of the endoscope 10 in each embodiment, but the invention can also be applied to a case in which a rigid endoscope is used. Furthermore, the endoscopes 10 are connected to the processors 12, 12A, and 12B by wires in the respective embodiments, but communication between the endoscope and the processor may be contactless communication (optical communication or the like).

EXPLANATION OF REFERENCES

9: endoscope apparatus
9A: endoscope apparatus
9B: endoscope apparatus
10: electronic endoscope (endoscope)
11: light source device
11A: light source device
11B: light source device
12: processor
12A: processor
12B: processor
13: monitor
15: insertion part
16: operation unit
17: universal cord
19: soft portion
20: bendable portion
21: tip portion
23: bending operation knob
24: air/water supply button
25: suction button
26: treatment tool inlet
28: light guide
29: signal cable
30A: connector
30B: connector
33: fluorescent dye
34: portion to be observed
36B: semiconductor light source
36B1: semiconductor light source
36B2: semiconductor light source
36G: semiconductor light source
36R: semiconductor light source
36V: semiconductor light source
37: dichroic filter
38: dichroic filter
38A: dichroic filter
39: lens
40: light source control unit
45: irradiation lens
46: illumination window
47: observation window
48: condenser lens
49: image pickup element
50: drive circuit
51: signal processing unit
52: image signal output unit
53: pixel
54: color filter
54B: color filter
54G: color filter
54R: color filter
55: drive control unit
56: image signal acquisition unit
57: image generating unit
58: display control unit
59: storage unit
60: observation image generating unit
61: fluorescence image generating unit
63: observation image
64: fluorescence image
64a: simple fluorescence image
64b: background image
66B: spectral transmittance characteristic
66G: spectral transmittance characteristic
66R: spectral transmittance characteristic
68: wavelength limiting filter
70: dichroic filter
72: narrow-band light image generating unit
74: narrow-band light image
80: oxygen saturation image
82: long-wavelength cut filter
83: short-wavelength cut filter
85: oxygen saturation image generating unit
B1: signal component
B2: signal component
BL: blue light
BL1: first blue light
BL2: second blue light Bb: signal component
Bf: signal component
EL: excitation light
ELx: narrow-band excitation light
FL: fluorescence
G1: signal component
G2: signal component
GL: green light
GLx: narrow-band green light
GR: reflected light
Gb: signal component
Gf: signal component
IC: resultant light-image pickup signal
IF: fluorescence-image pickup signal
IS: reflected light-image pickup signal
ISb: blue reflected light-image pickup signal
P1: first peak value
P2: second peak value
P3: third peak value
R1: signal component
R2: signal component
RL: red light
Rb: signal component
Rf: signal component
S1 to S5: method of operating endoscope apparatus
S10 to S19: method of operating endoscope apparatus
T1: period
T2: predetermined period
T3: period
VL: purple light
VR: reflected light
W: white light
W1: first wavelength region
W1A: first wavelength region
W2: second wavelength region
W2A: second wavelength region
W3: third wavelength region
W3A: third wavelength region
W4: fourth wavelength region
WR: reflected light

What is claimed is:

1. An endoscope apparatus performing illumination light observation that irradiates a portion to be observed with illumination light and observes the portion to be observed, and fluorescence observation that irradiates the portion to be observed with excitation light to allow a fluorescent material, which is contained in the portion to be observed, to be excited to emit light and observes fluorescence, the endoscope apparatus comprising:
 a light irradiation section that irradiates the portion to be observed with the illumination light and the excitation light while switching the illumination light and the excitation light, wherein the light irradiation section includes three or more types of semiconductor light sources of different wavelengths to simultaneously generate the illumination light;
 an image pickup unit that picks up an image using reflected light of the illumination light reflected from the portion to be observed and outputs a reflected light-image pickup signal in a case in which the portion to be observed is irradiated with the illumination light from the light irradiation section, and picks up an image using the fluorescence and outputs a fluorescence-image pickup signal in a case in which the portion to be observed is irradiated with the excitation light from the light irradiation section; and
 color filters that are provided in the image pickup unit, transmit the illumination light and the excitation light, and include a first color filter having a first spectral transmittance characteristic and a second color filter having a second spectral transmittance characteristic of which a peak of transmittance is closer to a long wavelength side than a peak of transmittance of the first spectral transmittance characteristic,
 wherein in a case in which a peak value of absorption intensity of the fluorescent material is referred to as a first peak value and a wavelength region where the absorption intensity of the fluorescent material is 10% or more of the first peak value is referred to as a first wavelength region, at least a part of a wavelength region of the excitation light is included in the first wavelength region,
 in a case in which a peak value of transmittance of the first spectral transmittance characteristic is referred to as a second peak value, a peak value of transmittance of the second spectral transmittance characteristic is referred to as a third peak value, a wavelength region where the transmittance of the first spectral transmittance characteristic is 60% or more of the second peak value is referred to as a second wavelength region, and a wavelength region where the transmittance of the second spectral transmittance characteristic is 40% or less of the third peak value is referred to as a third wavelength region, the wavelength region of the excitation light is included in the second wavelength region and the third wavelength region, and
 in a case in which a wavelength region where the transmittance of the second spectral transmittance characteristic is 80% or more of the third peak value is referred to as a fourth wavelength region, a wavelength at which intensity of the fluorescence is a peak is included in the fourth wavelength region.

2. The endoscope apparatus according to claim 1,
 wherein the first wavelength region is a wavelength region where the absorption intensity of the fluorescent material is 50% or more of the first peak value.

3. The endoscope apparatus according to claim 2,
 wherein the first wavelength region is included in a wavelength region of blue light, and the fluorescence is green fluorescence.

4. The endoscope apparatus according to claim 3,
 wherein the excitation light is blue light.

5. The endoscope apparatus according to claim 3,
 wherein a wavelength region of the first spectral transmittance characteristic and a wavelength region of the second spectral transmittance characteristic partially overlap each other.

6. The endoscope apparatus according to claim 1,
 wherein the first wavelength region is included in a wavelength region of blue light, and the fluorescence is green fluorescence.

7. The endoscope apparatus according to claim 6,
 wherein the excitation light is blue light.

8. The endoscope apparatus according to claim 7,
 wherein a wavelength region of the first spectral transmittance characteristic and a wavelength region of the second spectral transmittance characteristic partially overlap each other.

9. The endoscope apparatus according to claim 6,
 wherein a wavelength region of the first spectral transmittance characteristic and a wavelength region of the second spectral transmittance characteristic partially overlap each other.

10. The endoscope apparatus according to claim 1 wherein the second wavelength region is a wavelength region where the transmittance of the first spectral transmittance characteristic is 80% or more of the second peak value.

11. The endoscope apparatus according to claim 1, wherein the third wavelength region is a wavelength region where the transmittance of the second spectral transmittance characteristic is 20% or less of the third peak value.

12. The endoscope apparatus according to claim 1, wherein the three or more types of semiconductor light sources emit three or more types of the excitation light that are included in a wavelength region corresponding to a bluish color including purple and blue and have peak wavelengths of light intensity different from each other.

13. The endoscope apparatus according to claim 12, wherein the semiconductor light source includes a first semiconductor light source that emits purple light, a second semiconductor light source that emits first blue light of a short wavelength-side wavelength region obtained in a case in which a wavelength region corresponding to a wavelength longer than a predetermined wavelength is cut out of a wavelength region of blue light, and a third semiconductor light source that emits second blue light of a long wavelength-side wavelength region obtained in a case in which a wavelength region corresponding to a wavelength shorter than the predetermined wavelength is cut out of the wavelength region of the blue light, and the light irradiation section emits the purple light, which is emitted from the first semiconductor light source, and the first blue light, which is emitted from the second semiconductor light source, as the illumination light and emits the first blue light, which is emitted from the second semiconductor light source, and the second blue light, which is emitted from the third semiconductor light source, as the excitation light.

14. The endoscope apparatus according to claim 13, wherein the illumination light is white light, the light irradiation section has a special emission mode in which the white light including the second blue light and the second blue light are emitted to the portion to be observed while being switched, and the image pickup unit picks up an image using reflected light of the white light and outputs the reflected light-image pickup signal and picks up an image using reflected light of the second blue light and outputs a blue reflected light-image pickup signal in a case in which the light irradiation section is in the special emission mode, and the endoscope apparatus further comprises an oxygen saturation image generating unit that generates an oxygen saturation image representing oxygen saturation of the portion to be observed on the basis of the reflected light-image pickup signal and the blue reflected light-image pickup signal output from the image pickup unit.

15. The endoscope apparatus according to claim 12, wherein the semiconductor light source is a light emitting diode.

16. The endoscope apparatus according to claim 1, wherein in a case in which the excitation light is blue light and the fluorescence is red fluorescence, a wavelength region of the first spectral transmittance characteristic and a wavelength region of the second spectral transmittance characteristic are separated from each other.

17. The endoscope apparatus according to claim 1, wherein the first color filter and the second color filter are primary color filters.

18. The endoscope apparatus according to claim 1, further comprising a fluorescence image generating unit that generates a fluorescence image of the portion to be observed on the basis of the reflected light-image pickup signal and the fluorescence-image pickup signal output from the image pickup unit.

19. The endoscope apparatus according to claim 1, wherein the image pickup unit includes an image pickup element that includes a plurality of two-dimensionally arranged pixels and the color filters, and the endoscope apparatus further comprising a drive control unit for the image pickup element that makes a time, in which electrical charges are accumulated in the pixels of the image pickup element in a case where the portion to be observed is irradiated with the excitation light from the light irradiation section, be longer than a time in which electrical charges are accumulated in the pixels of the image pickup element in a case where the portion to be observed is irradiated with the illumination light from the light irradiation section.

20. A method of operating an endoscope apparatus including a light irradiation section that selectively irradiates a portion to be observed with illumination light and excitation light, wherein the light irradiation section includes three or more types of semiconductor light sources of different wavelengths to simultaneously generate the illumination light, and an image pickup unit that includes color filters including a first color filter having a first spectral transmittance characteristic and a second color filter having a second spectral transmittance characteristic of which a peak of transmittance is closer to a long wavelength side than a peak of transmittance of the first spectral transmittance characteristic, the endoscope apparatus performing illumination light observation that irradiates the portion to be observed with the illumination light from the light irradiation section and observes the portion to be observed, and fluorescence observation that irradiates the portion to be observed with the excitation light from the light irradiation section to allow a fluorescent material, which is contained in the portion to be observed, to be excited to emit light and observes fluorescence, wherein the light irradiation section irradiates the portion to be observed with the illumination light and the excitation light while switching the illumination light and the excitation light, the image pickup unit picks up an image using reflected light of the illumination light reflected from the portion to be observed and outputs a reflected light-image pickup signal in a case in which the portion to be observed is irradiated with the illumination light from the light irradiation section, and picks up an image using the fluorescence and outputs a fluorescence-image pickup signal in a case in which the portion to be observed is irradiated with the excitation light from the light irradiation section, in a case in which a peak value of absorption intensity of the fluorescent material is referred to as a first peak value and a wavelength region where the absorption intensity of the fluorescent material is 10% or more of the first peak value is referred to as a first wavelength region, at least a part of a wavelength region of the excitation light is included in the first wavelength region, in a case in which a peak value of transmittance of the first spectral transmittance characteristic is referred to as a second peak value, a peak value of transmittance of the second spectral transmittance characteristic is referred to as a third peak value, a wavelength region where the transmittance of the first spectral transmittance characteristic is 60% or more of the second peak value is referred to as a second wavelength region, and a wavelength region where the transmittance of the second spectral transmittance characteristic is 40% or less of the third peak value is referred to as a third wavelength region, the wavelength region of the excitation light is included in the second wavelength region and the third wavelength region, and in a case in which a wavelength region where the transmittance of the second spectral transmittance characteristic is 80% or more of the third peak value is referred to as a fourth wavelength region, a wavelength at which intensity of the fluorescence is a peak is included in the fourth wavelength region.

* * * * *